(12) United States Patent
Sivan et al.

(10) Patent No.: US 9,028,664 B2
(45) Date of Patent: *May 12, 2015

(54) PROTON CONCENTRATION TOPOGRAPHIES, METHODS AND DEVICES FOR PRODUCING THE SAME

(75) Inventors: Uri Sivan, Haifa (IL); Elad Brod, Tivon (IL)

(73) Assignee: Technion Research & Development Foundation Limited, Haifa (IL)

( * ) Notice: Subject to any disclaimer, the term of this patent is extended or adjusted under 35 U.S.C. 154(b) by 88 days.

This patent is subject to a terminal disclaimer.

(21) Appl. No.: 13/390,352

(22) PCT Filed: Aug. 18, 2010

(86) PCT No.: PCT/IL2010/000672
§ 371 (c)(1),
(2), (4) Date: Feb. 14, 2012

(87) PCT Pub. No.: WO2011/021196
PCT Pub. Date: Feb. 24, 2011

(65) Prior Publication Data
US 2012/0138468 A1    Jun. 7, 2012

Related U.S. Application Data

(60) Provisional application No. 61/272,110, filed on Aug. 18, 2009.

(51) Int. Cl.
*G01N 27/447* (2006.01)
*B01D 57/02* (2006.01)
(Continued)

(52) U.S. Cl.
CPC .......... *G01N 27/44795* (2013.01); *B01D 57/02* (2013.01); *B01D 61/445* (2013.01); *C07K 1/28* (2013.01); *G01N 21/80* (2013.01); *G01N 27/44747* (2013.01); *G01N 27/44773* (2013.01)

(58) Field of Classification Search
CPC ........ G01N 27/447; C07K 1/28; B01L 57/02; B01L 61/445
USPC ......... 204/450, 458, 459, 600, 610, 644, 537, 204/548, 631; 435/287.1
See application file for complete search history.

(56) References Cited

U.S. PATENT DOCUMENTS

| 4,868,130 A | 9/1989 | Hargreaves |
| 4,900,414 A | 2/1990 | Sibalis |

(Continued)

FOREIGN PATENT DOCUMENTS

| CN | 1462368 | 12/2003 |
| CN | 1549924 | 11/2004 |

(Continued)

OTHER PUBLICATIONS

Communication Pursuant to Rules 70(2) and 70a(2) EPC and Reference to Rule 39(1) EPC Dated Apr. 8, 2013 From the European Patent Office Re. Application No. 12177368.3.
(Continued)

*Primary Examiner* — Jennifer Dieterle

(57) ABSTRACT

A device for isoelectric focusing. The device comprises a focusing container configured to contain an electrolyte solution and having a longitudinal axis and at least one electrolysis unit mounted in a close proximity to the longitudinal axis. Each electrolysis unit injects an ion flow into the focusing container so as to create a pH gradient having a plurality of steps in the electrolyte solution, along the longitudinal axis. Each step has a substantially uniform pH level and the pH gradient is defined by at least one pH ramp between every two sequential steps of the plurality of steps.

14 Claims, 13 Drawing Sheets
(11 of 13 Drawing Sheet(s) Filed in Color)

(51) Int. Cl.
B01D 61/44 (2006.01)
C07K 1/28 (2006.01)
G01N 21/80 (2006.01)

(56) References Cited

U.S. PATENT DOCUMENTS

| | | | |
|---|---|---|---|
| 5,091,070 | A | 2/1992 | Bauer et al. |
| 5,110,434 | A | 5/1992 | Zhu et al. |
| 5,646,001 | A | 7/1997 | Terstappen et al. |
| 6,296,752 | B1 | 10/2001 | McBride et al. |
| 6,824,740 | B1 | 11/2004 | Sheldon, III et al. |
| 7,166,202 | B2 * | 1/2007 | Bukshpan et al. ............ 204/459 |
| 8,366,899 | B2 * | 2/2013 | Albrecht et al. ............. 204/548 |
| 2001/0023825 | A1 * | 9/2001 | Frumin et al. ................ 204/458 |
| 2003/0102215 | A1 | 6/2003 | Bukshpan et al. |
| 2004/0101973 | A1 | 5/2004 | Weber |
| 2004/0231986 | A1 * | 11/2004 | Rossier et al. ................ 204/450 |
| 2005/0189237 | A1 | 9/2005 | Sano |
| 2005/0284762 | A1 * | 12/2005 | Astorga-Wells et al. ..... 204/451 |
| 2006/0029978 | A1 | 2/2006 | O'Neill et al. |
| 2006/0137603 | A1 | 6/2006 | Bukshpan |
| 2006/0169575 | A1 | 8/2006 | Sumita |
| 2012/0145548 | A1 | 6/2012 | Sivan et al. |

FOREIGN PATENT DOCUMENTS

| | | |
|---|---|---|
| CN | 1558460 | 12/2004 |
| CN | 101294930 | 10/2008 |
| EP | 688395 | 8/2006 |
| JP | 2002-265494 | 9/2002 |
| JP | 2006-213932 | 8/2006 |
| JP | 2007-190548 | 8/2007 |
| WO | WO 91/17815 | 11/1991 |
| WO | WO 02/25263 | 3/2002 |
| WO | WO 03/008977 | 1/2003 |
| WO | WO 2005/021841 | 3/2005 |
| WO | WO 2007/093395 | 8/2007 |
| WO | WO 2008/112253 | 9/2008 |
| WO | WO 2008/131328 | 10/2008 |
| WO | WO2009/002459 | * 12/2008 |
| WO | WO 2009/002459 | 12/2008 |
| WO | WO 2009/027970 | 3/2009 |
| WO | WO 2011/021196 | 2/2011 |

OTHER PUBLICATIONS

Translation of Office Action Dated May 2, 2012 From the State Intellectual Property Office of the People's Republic of China Re. Application No. 200880114690.6.
Official Action Dated Jun. 6, 2013 From the US Patent and Trademark Office Re. U.S. Appl. No. 12/675,794.
Translation of Reason for Rejection Dated Jul. 2, 2013 From the Japanese Patent Office Re. Application No. 2010-522513.
Invitation Pursuant to Rule 62a(1) EPC Dated Nov. 23, 2012 From the European Patent Office Re. Application No. 12177368.3.
Official Action Dated Nov. 16, 2012 From the US Patent and Trademark Office Re. U.S. Appl. No. 12/675,794.
International Preliminary Report on Patentability Dated Mar. 1, 2012 From the International Bureau of WIPO Re. Application No. PCT/IL2010/000672.
Office Action Dated Jan. 14, 2013 From the Israel Patent Office Re. Application No. 204182 and Its Translation Into English.
Communication Pursuant to Article 94(3) EPC Dated Jul. 20, 2010 From the European Patent Office Re. Application No. 08789831.8.
Communication Pursuant to Article 94(3) EPC Dated Mar. 24, 2011 From the European Patent Office Re. Application No. 08789831.8.
Communication Pursuant to Article 94(3) EPC Dated Jul. 26, 2011 From the European Patent Office Re. Application No. 08789831.8.
Communication Pursuant to Article 94(3) EPC Dated Sep. 28, 2010 From the European Patent Office Re. Application No. 08789831.8.
Communication Relating to the Results of the Partial International Search Dated Dec. 20, 2010 From the International Searching Authority Re. Application No. PCT/IL2010/000672.

International Preliminary Report on Patentability Dated Mar. 2, 2010 From the International Bureau of WIPO Re.: Application No. PCT/IL2008001159.
International Search Report and the Written Opinion Dated Apr. 7, 2009 From the International Searching Authority Re.: Application No. PCT/IL2008/001159.
International Search Report and the Written Opinion Dated Dec. 10, 2010 From the International Searching Authority Re.: Application No. PCT/IL2010/000671.
International Search Report and the Written Opinion Dated Mar. 24, 2011 From the International Searching Authority Re.: Application No. PCT/IL2010/000672.
Response Dated Jul. 4, 2011 to Communication Pursuant to Article 94(3) EPC of Mar. 24, 2011 From the European Patent Office Re. Application No. 08789831.8.
Response Dated Mar. 9, 2011 to Communication Pursuant to Article 94(3) EPC of Sep. 28, 2010 From the European Patent Office Re. Application No. 08789831.8.
Response Dated Sep. 16, 2010 to Communication Pursuant to Article 94(3) EPC of Jul. 20, 2010 From the European Patent Office Re. Application No. 08789831.8.
Response Dated Nov. 21, 2011 to Communication Pursuant to Article 94(3) EPC of Jul. 26, 2011 From the European Patent Office Re. Application No. 08789831.8.
Translation of Office Action Dated Nov. 9, 2011 From the State Intellectual Property Office of the People's Republic of China Re. Application No. 200880114690.6.
Britz-McKibbin et al. "Selective Focusing of Catecholamines and Weakly Acidic Compounds by Capillary Electrophoresis Using a Dynamic pH Junction", Analytical Chemistry, XP002611194, 72(6): 1242-1252, Mar. 15, 2000. p. 1250, col. 1, Line 22—p. 1251, col. 1, Line 1, Fig.9.
Pabst et al. "Separation of Protein Charge Variants With Induced pH Gradients Using Anion Exchange Chromatographic Columns", Biotechnology Progress, XP002611195, 24(5): 1096-1106, Sep. 2008. Abstract, P1100, col. 1, Lines 12-16.
Wu et al. "Isoelectric Focusing Sample Injection for Capillary Electrophoresis of Proteins", Electrophoresis, XP002611196, 26(3): 563-570, Feb. 2005. Abstract, p. 565, col. 2, Last §—p. 566, col. 1, Last §, p. 567, col. 1, Line 17—col. 2, Line 11, Fig.3B.
Wu et al. "Miniaturization of Capillary Isoelectric Focusing", Electrophoresis, XP003008375, 22: 3968-3971, Jan. 1, 2001. Abstract, p. 3669, col. 2, Line 1—p. 3970, col. 1, Last Line, Figs.1, 3, 4.
International Preliminary Report on Patentability Dated Mar. 1, 2012 From the International Bureau of WIPO Re. Application No. PCT/IL2011/000671.
Examiner's Report Dated Feb. 27, 2012 From the Australian Government, IP Australia Re. Application No. 2008293381.
Translation of Notice of Reason for Rejection Dated Jul. 27, 2012 From the Japanese Patent Office Re. Application No. 2010-522513.
Translation of Notification of Office Action Dated Jul. 29, 2013 From the State Intellectual Property Office of the People's Republic of China Re. Application No. 201080036972.6.
Translation of Search Report Dated Jul. 29, 2013 From the State Intellectual Property Office of the People's Republic of China Re. Application No. 201080036972.6.
Restriction Official Action Dated Nov. 12, 2013 From the US Patent and Trademark Office Re. U.S. Appl. No. 13/390,539.
Notification of the Office Action Dated Sep. 18, 2013 From the State Intellectual Property Office of the People's Republic of China Re. Application No. 201080036971.1 and Its Translation Into English.
Search Report Dated Sep. 18, 2013 From the State Intellectual Property Office of the People's Republic of China Re. Application No. 201080036971.1 and Its Translation Into English.
Translation of Notice of Reason for Rejection Dated Sep. 20, 2013 From the Japanese Patent Office Re. Application No. 2012-525252.
Communication Under Rule 71(3) EPC Dated Oct. 11, 2013 From the European Patent Office Re. Application No. 08789831.8.
Partial European Search Report and the European Search Opinion Dated Mar. 5, 2013 From the European Patent Office Re. Application No. 12177368.3.

(56) References Cited

OTHER PUBLICATIONS

Huang et al. "Capillary Isoelectric Focusing Without Carrier Ampholytes", Analytical Chemistry, XP002584974, 72(19): 4758-4761, Oct. 1, 2000. Abstract, Fig. 1.
Restriction Official Action Dated Sep. 19, 2012 From the US Patent and Trademark Office Re. U.S. Appl. No. 12/675,794.
Dismissal of Amendment Dated Mar. 14, 2014 From the Japanese Patent Office Re. Application No. 2010-522513 and Its Translation Into English.
Official Decision of Rejection Dated Mar. 14, 2014 From the Japanese Patent Office Re. Application No. 2010-522513 and Its Translation Into English.
Notification of the Office Action Dated May 8, 2014 From the State Intellectual Property Office of the People's Republic of China Re. Application No. 201080036971.1 and Its Translation Into English.
Notice of Reason for Rejection Dated Jan. 7, 2014 From the Japanese Patent Office Re. Application No. 2012-525253 and Its Translation Into English.
Office Action Dated Feb. 20, 2014 From the State Intellectual Property Office of the People's Republic of China Re. Application No. 201210450797.6 and Its Translation Into English.
Search Report Dated Feb. 20, 2014 From the State Intellectual Property Office of the People's Republic of China Re. Application No. 201210450797.6 and Its Translation Into English.
Communication Under Rule 71(3) EPC Dated Feb. 4, 2014 From the European Patent Office Re. Application No. 12177368.3.
Notification of Office Action Dated Jan. 9, 2014 From the State Intellectual Property Office of the People's Republic of China Re. Application No. 201080036972.6 and Its Translation Into English.
Official Action Dated Jul. 11, 2014 From the US Patent and Trademark Office Re. U.S. Appl. No. 12/675,794.
Notice of Allowance Dated Jun. 18, 2014 From the US Patent and Trademark Office Re. U.S. Appl. No. 13/390,539.
Notice of Reason for Rejection Dated Jun. 6, 2014 From the Japanese Patent Office Re. Application No. 2012-525252 and Its Translation Into English.
Patent Examination Report Dated Jun. 5, 2014 From the Australian Government, IP Australia Re. Application No. 2010286046.
Official Action Dated Jan. 23, 2014 From the US Patent and Trademark Office Re. U.S. Appl. No. 13/390,539.
Notice of Reason for Rejection Dated Sep. 26, 2014 From the Japanese Patent Office Re. Application No. 2010-522513 and Its Translation Into English.
Patent Examination Report Dated Jul. 30, 2014 From the Australian Government, IP Australia Re. Application No. 2010286047.
Official Action Dated Sep. 10, 2013 From the US Patent and Trademark Office Re. U.S. Appl. No. 13/669,023.
De Jong et al. "Membranes and Microfluidics: A Review", Lab on a Chip, 6(9): 1125-1139, Sep. 2006.

\* cited by examiner

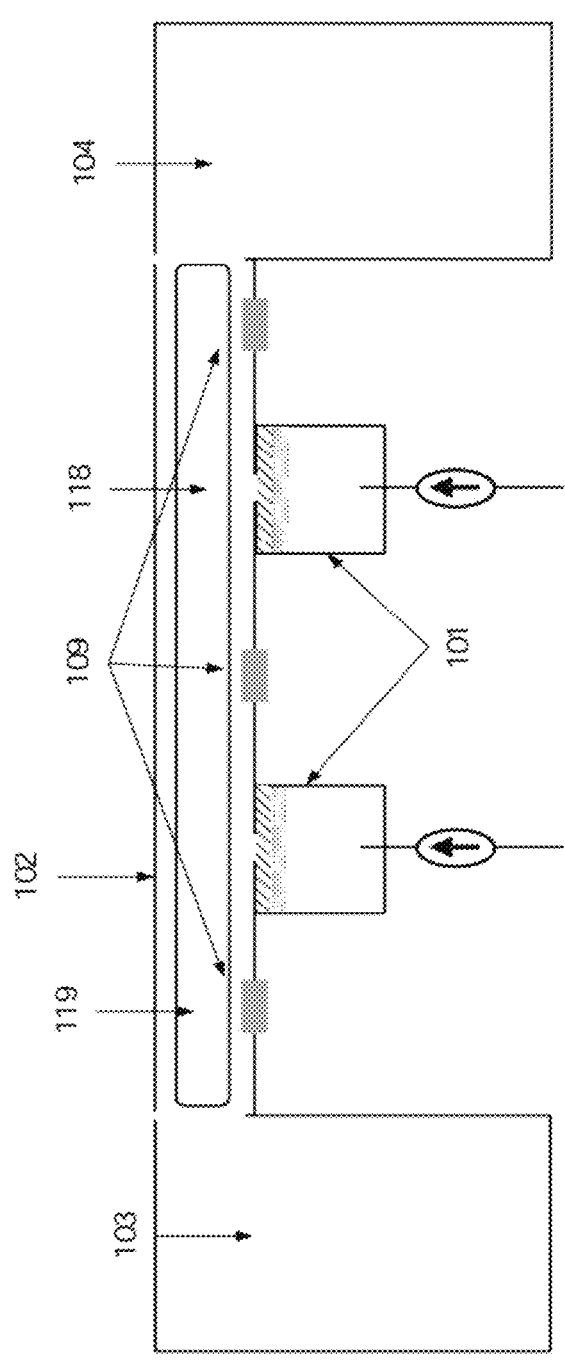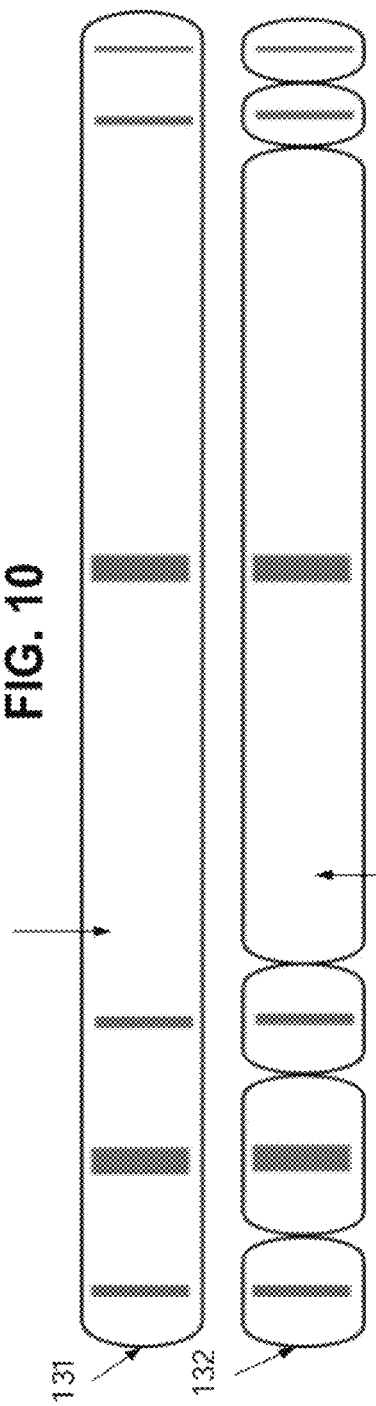
FIG. 10
FIG. 11

PROTON CONCENTRATION TOPOGRAPHIES, METHODS AND DEVICES FOR PRODUCING THE SAME

RELATED APPLICATION/S

The content of International Patent Application Publication No. WO 2009/027970, published on Mar. 5, 2009, is incorporated by reference as if fully set forth herein.

This application is a National Phase of PCT Patent Application No. PCT/IL2010/000672 having International filing date of Aug. 18, 2010, which claims the benefit of priority of U.S. Provisional Patent Application No. 61/272,110 filed on Aug. 18, 2009. The contents of the above applications are all incorporated herein by reference.

FIELD AND BACKGROUND OF THE INVENTION

The present invention, in some embodiments thereof, relates to molecular analysis and separation and, more particularly, but not exclusively, to methods and system for isoelectric focusing.

Isoelectric focusing is an analytical technique for separating molecules in an analyte sample by taking advantage of the differing ionic properties of the molecules.

Isoelectric focusing is usually performed in an electrolyte solution, optionally in a gel form, for example based on polyacrylamide, starch and/or agarose, having an immobilized proton concentration gradient, generally the proton concentration gradient changing from higher to lower pH in a given direction. In some implementation solutions which contain ampholytes which, under an electric field, generate a pH gradient. In isoelectric focusing, the separation takes place in a pH gradient that occupies the whole separation distance and is arranged so that the pH in the gradient increases from anode towards the cathode. In use, the analyte is loaded onto some location on the electrolyte solution. The charge of each different molecule changes in response to the ambient proton concentration according to the acidity (pKa) of the various functional groups of the molecule.

An electric potential is applied parallel to the proton concentration gradient between an isoelectric focusing anode and isoelectric focusing cathode. Molecules having a net positive charge migrate through the electrolyte solution towards the cathode while molecules having a net negative charge migrate through the electrolyte solution towards the anode.

As the molecules migrate, the ambient pH changes to reduce the net charge on the molecule until the molecule reaches an isoelectric point (pI) where, due to the ambient pH, the net charge on the molecule is zero. In this point the migrating molecule stops since they have zero charge. In such a manner, isoelectric focusing focuses molecules having a certain pI into a relatively narrow volume of the electrolyte solution. Isoelectric focusing is useful for the analysis of proteins by characterizing them according to their acidities. More importantly, it is useful for separation of protein mixtures.

International Patent Application Publication No. WO 2009/027970, published on Mar. 5, 2009 and incorporated herein by reference, describes methods and devices useful in producing local concentrations of protons, proton concentration gradients and desired proton concentration topographies in an environment, such as an electrolyte solution, a gel, or the like, including an electrolyte. This application also discloses methods and devices for isoelectric focusing and for display of data.

SUMMARY OF THE INVENTION

According to some embodiments of the present invention there is provided a device for isoelectric focusing. The device comprises a focusing container having a longitudinal axis and configured to contain an electrolyte solution and at least one electrolysis unit, mounted in a close proximity to the longitudinal axis. Each electrolysis unit is configured to inject an ion flow into the focusing container so as to create a pH gradient having a plurality of steps in the electrolyte solution along the longitudinal axis. Each step having a substantially uniform pH level and the pH gradient is defined by at least one pH ramp between every two sequential steps of the plurality of steps.

Optionally, the pH ramp is of at least 0.1 pH.

Optionally, each step is at least 3 mm long.

Optionally, the at least one electrolysis unit comprises a plurality of electrolysis units, further comprising a controller for separately controlling each electrolysis unit.

Optionally, the electrolyte solution comprises a plurality of biomolecules, the plurality of biomolecules concentrate only at the at least one pH ramp along the pH gradient.

Optionally, the gradient comprises less than 10 of the plurality of steps.

Optionally, the gradient comprises less than 5 of the plurality of steps.

Optionally, the gradient comprises two of the plurality of steps.

Optionally, one of the at least one electrolysis unit is configured to inject a plurality of Hydroxyl ions and another of the at least one electrolysis unit being configured to inject a plurality of Hydrogen ions.

Optionally, the focusing container has a plurality of narrowed segments. Each electrolysis unit being configured to inject the ion flow in a respective the narrow segment.

According to some embodiments of the present invention there is provided a device for isoelectric focusing. The device comprises a focusing container configured to contain an electrolyte solution and having first and second ends and a longitudinal axis, the focusing container having at least one slit along the first and second ends and an anode and a cathode respectively mounted at the first end and the second end and configured to pass a first electric current therebetween via the electrolyte solution. The device further includes at least one bipolar membrane each mounted in a close proximity to the at least one slit and at least one controllable electrode each mounted in front of a respective at least one bipolar and configured for applying a second electric current on the at least one respective bipolar membrane so as to promote an ion flow via the at least one slit.

Optionally, the device comprises a current source supplying the first and second electric current respectively to the anode and cathode and to the at least one controllable electrode.

More optionally, the device further comprises a Wheatstone bridge physically connected to the controllable electrode via a generator current source.

Optionally, the first and second electric currents are high voltage electric currents.

Optionally, the at least one bipolar membrane is at least one bubbleless bipolar membrane.

Optionally, the device comprises first and second receptacles each respectively connected to the first the second ends, the anode and the cathode being respectively at least partly mounted in the first and second receptacles.

Optionally, the device comprises a supporting structure having a plurality of sockets in front of niche for supporting the focusing container. Each socket contains one of the at least one bipolar membrane and one of the at least one controllable electrode.

Optionally, the device comprises at least one pH probe configured for measuring a pH level in a proximity to a respective of the at least one bipolar membrane.

Optionally, the width of the at least one slit is less than 3 mm.

Optionally, the distance between the at least one controllable electrode and the bipolar membrane is less than 3 mm.

According to some embodiments of the present invention there is provided a method for isoelectric focusing. The method comprises providing a focusing container having a longitudinal axis, adding an electrolyte solution having a plurality of biomolecules to the container, applying an electric field on the electrolyte solution along the longitudinal axis, and injecting an ion flow in at least one point along the longitudinal axis to establish a pH gradient defined by a plurality of steps in the electrolyte solution so that the plurality of biomolecules accumulate in at least one concentration in proximity to the at least one point, Each step having a substantially uniform pH level, the pH gradient being defined by at least one pH ramp between every two sequential steps of the plurality of steps.

Optionally, the method further comprises adding a buffer for stabilizing the pH gradient.

Optionally, the pH gradient is defined by a plurality of ramps among the plurality of steps, further comprising adding a mixture of buffers for stabilizing the pH gradient.

Optionally, the plurality of biomolecules accumulate only in the at least one concentration.

Optionally, the injecting comprises applying a current on at least one bipolar membrane each mounted in a close proximity to the electrolyte solution at a respective the at least one point.

Optionally, the method further comprises diagnosing the plurality of biomolecules according to the at least one concentration.

Optionally, the method further comprises separately harvesting at least one of the at least one concentration.

According to some embodiments of the present invention there is provided a method for isoelectric focusing. The method comprises providing a container having an electrolyte solution with at least one biomolecule, adding at least one pH indicator to the electrolyte solution, and creating a pH gradient in the electrolyte solution. The method further comprises capturing at least one image of the electrolyte solution, computing at least one color property of at least a segment of the electrolyte solution according to the at least one image, and calculating at least one pH level in the segment according to the at least one color property.

According to some embodiments of the present invention there is provided a device for isoelectric focusing. The device comprises a focusing container configured to detachably hold a porous block wetted with electrolyte solution with a mixture of biomolecules along a longitudinal axis thereof, a plurality of electrodes configured to pass a first electric current via the electrolyte solution in the porous block, and at least one electrolysis unit mounted in a close proximity to the longitudinal axis each configured to inject an ion flow into the focusing container so as to change a pH gradient in the electrolyte solution in the porous block. The mixture of biomolecules is arranged in the porous block according to the pH gradient.

Optionally, the focusing container having an opening for at least one of placing the porous block in the focusing container and extracting the porous block from the focusing container.

According to some embodiments of the present invention there is provided a method for isoelectric focusing. The method comprises placing a porous block wetted with electrolyte solution with a mixture of biomolecules in a focusing container, creating a pH gradient in the electrolyte solution so at to promote a plurality of concentrations of the biomolecules in the porous block, and segmenting the porous block to a plurality of segments each separately containing one of the plurality of concentrations.

Optionally, the segmenting is performed by pinching the porous block between each two of the plurality of concentrations to create the plurality of segments.

According to some embodiments of the present invention there is provided a removable solution cartridge for isoelectric focusing. The removable solution cartridge comprises a porous block sized and shaped to fit into a focusing channel of an isoelectric focusing system and configured to be wetted with an electrolyte solution having a plurality of biomolecules so as to allow a migration of the plurality of biomolecules according to a pH gradient formed in the electrolyte solution.

Optionally, the porous block may be pinched to create a plurality of segments each comprising a single concentration of the plurality of biomolecules.

According to some embodiments of the present invention there is provided a device for separating a mixture of proteins. The device comprises an electrophoresis container configured to contain an electrolyte solution and the mixture, the electrophoresis container having a longitudinal axis and first and second opposing sides parallel to the longitudinal axis, first and second bipolar membranes each respectively mounted on the first and second sides, the at least one electrode for applying an electric field on the electrolyte solution so as to motivate the proteins along the longitudinal axis. The one of the first and second bipolar membranes is configured to inject an ion flow into the electrophoresis container so as to create a pH gradient having a plurality of steps in the electrolyte solution in perpendicular to the longitudinal axis. Each step has a substantially uniform pH level.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic illustration of a lateral view of an exemplary isoelectric focusing device for separating biomolecules and/or diagnosing an analyte having one or more biomolecules, according to some embodiments of the present invention;

FIG. 2 is a blow up of a pH generator that is depicted FIG. 1, according to some embodiments of the present invention;

FIG. 3 is a schematic illustration of an exemplary structure for supporting some of the elements of the device depicted in FIG. 1, according to some embodiments of the present invention;

FIG. 4 is flowchart of a method for isoelectric focusing, according to some embodiments of the present invention;

FIG. 5 is a schematic illustration of a focusing channel having narrowed segments for increasing electric field in proximity to ion slits, according to some embodiments of the present invention;

FIG. 6 is a segment of a focusing channel positioned in proximity to a pH generator and the step shaped gradient when using $Na_2SO_4$ electrolyte solution and a phosphate buffer system ($HPO_4^{-2}/H_2PO_4^-$), according to some embodiments of the present invention;

FIG. 7 is an exemplary gradient having a graded pH profile which is created according to some embodiments of the present invention and concentrations of proteins;

FIG. 8 is a schematic illustration of a response of a bubbleless BPM to a passing current, according to some embodiments of the present invention;

FIG. 9 is a pH generator having a wide slit, according to some embodiments of the present invention;

FIG. 10 is a schematic illustration of a device, similar to the device depicted in FIG. 1, with a porous block wetted with electrolyte solution and biomolecules, according to some embodiments of the present invention;

FIG. 11 is a schematic illustration of an exemplary detachable porous block used for isolating biomolecule concentrations, according to some embodiments of the present invention;

Figure 12:
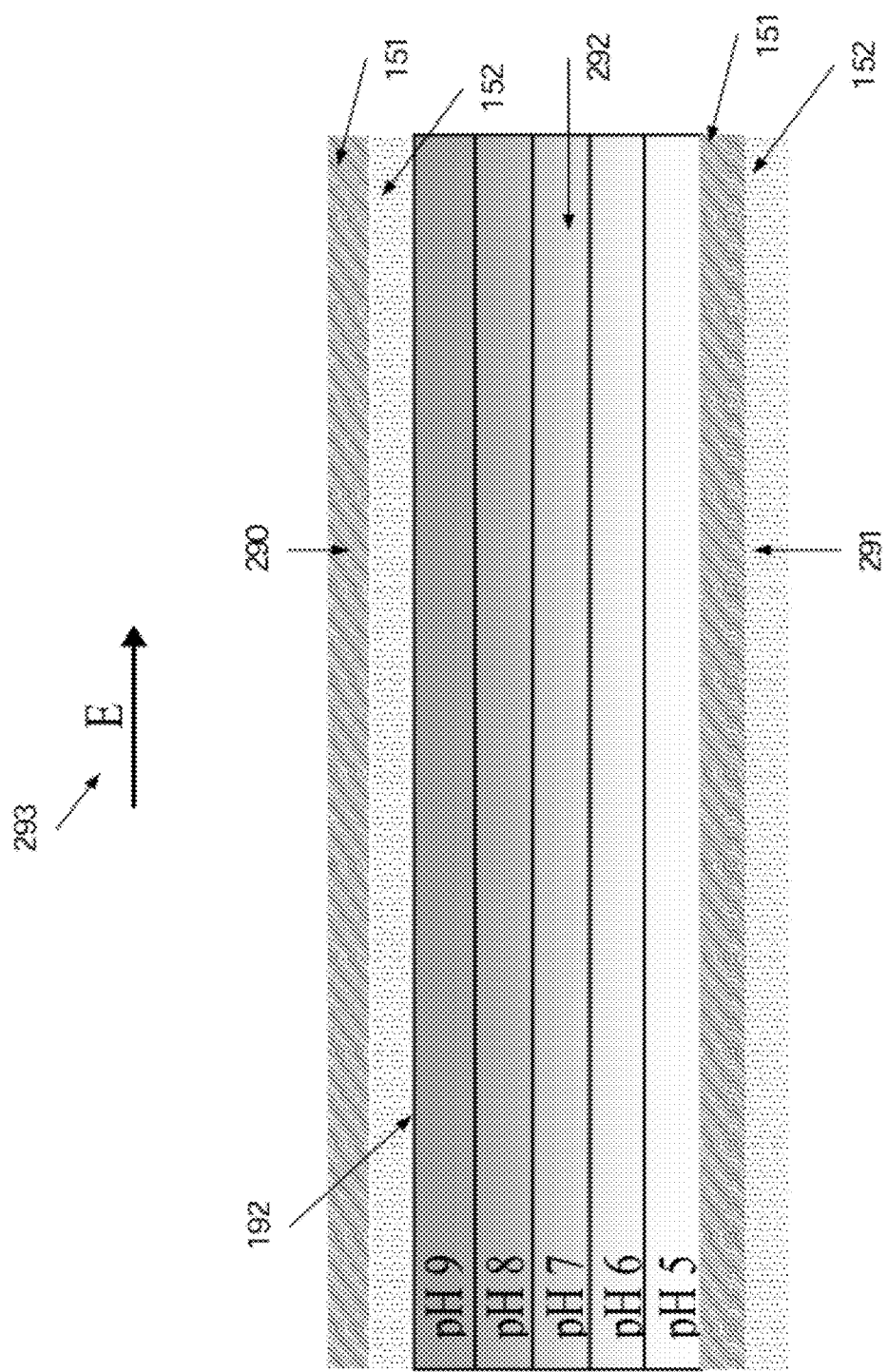

FIG. 12 is a schematic illustration of an electrophoresis container having bipolar membranes in opposing sides, which is designed to create a pH grading, according to some embodiments of the present invention.

Figure 13:
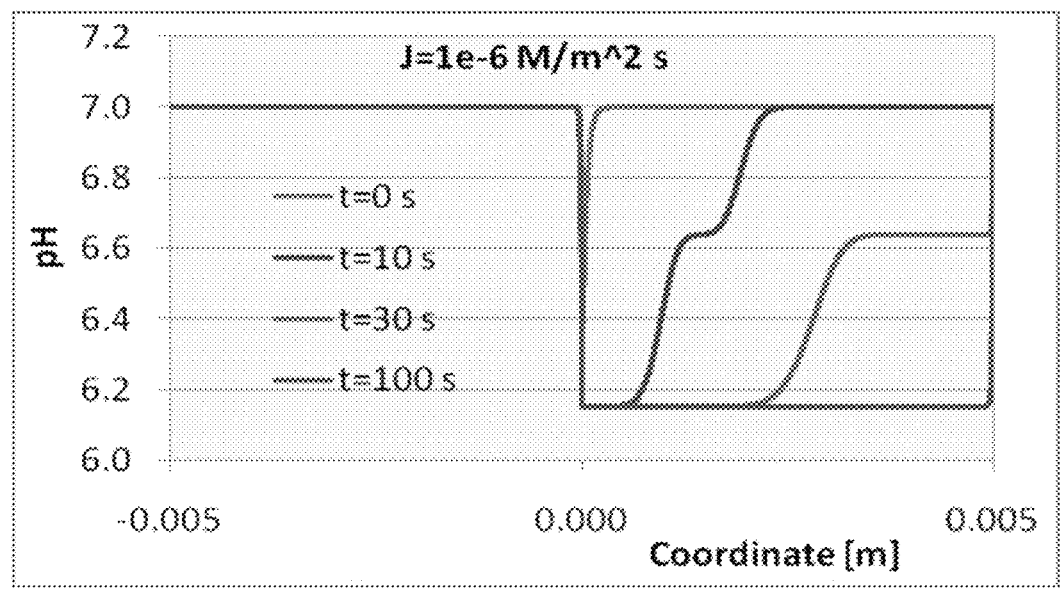
Figure 14:
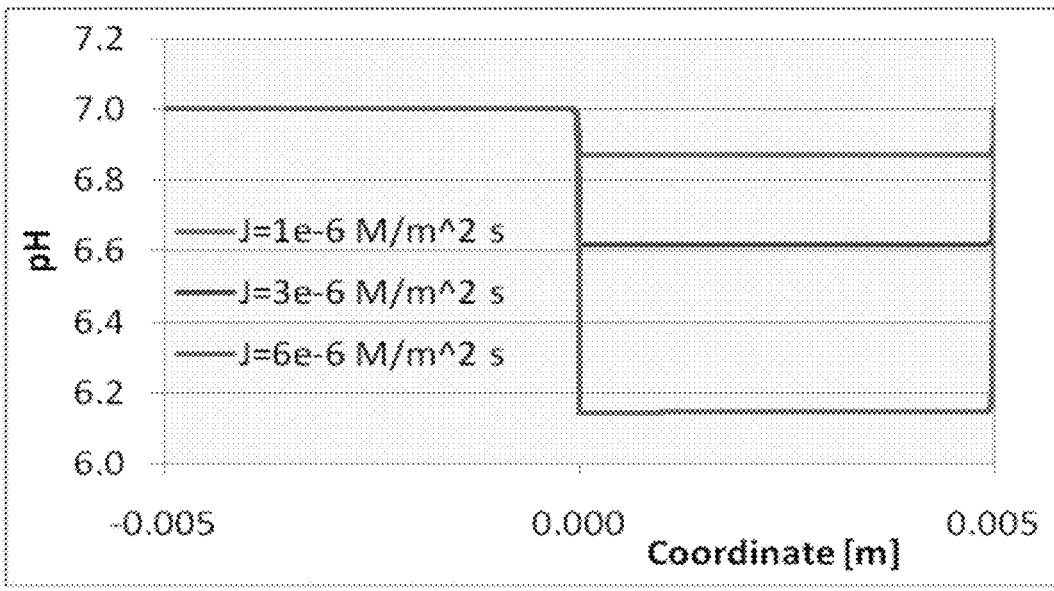
Figure 15:
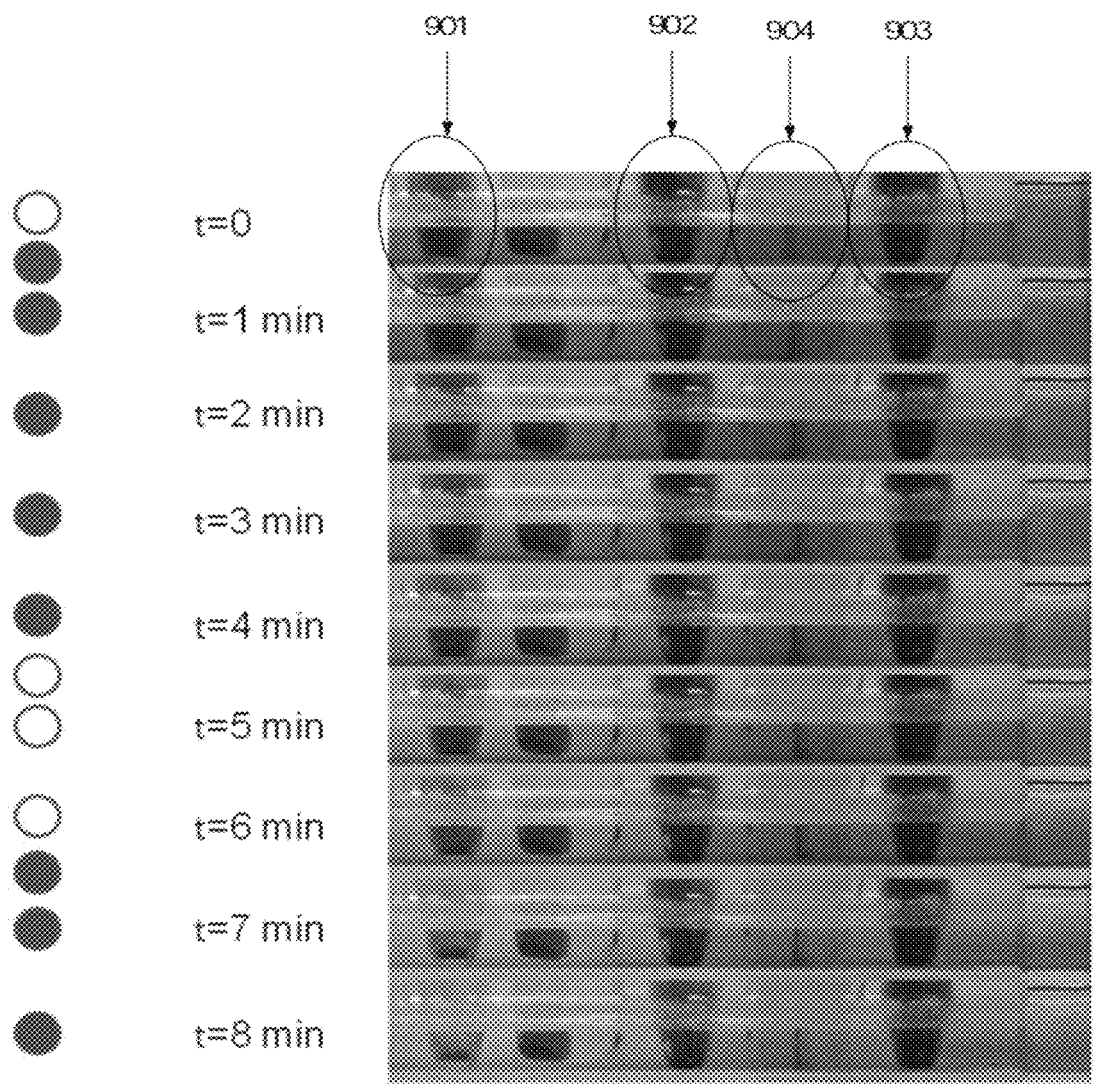
Figure 16:
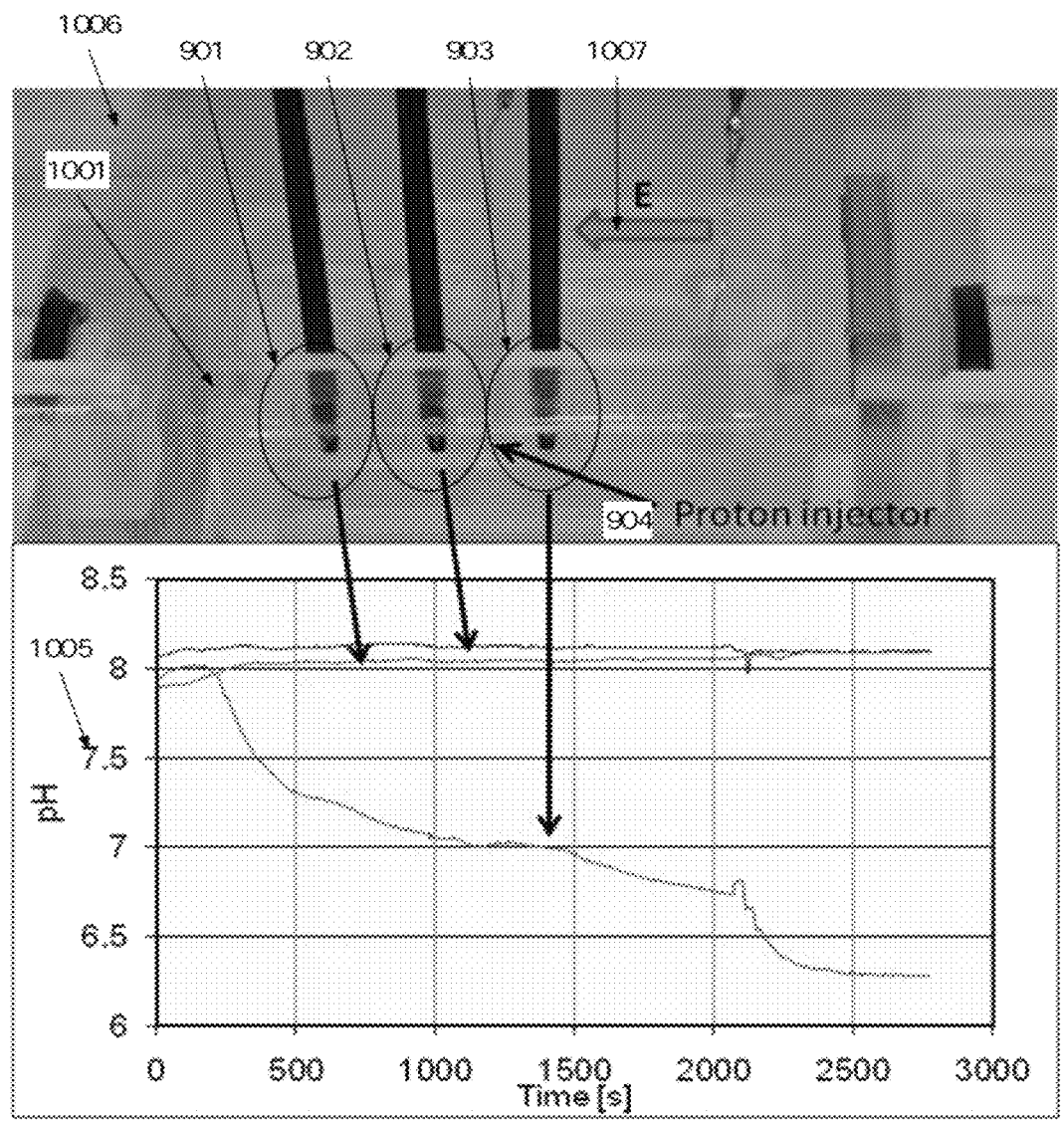

FIGS. 13 and 14 are graphs depicting various pH profiles generated by a simulation of an exemplary focusing device that is defined according to some embodiments of the present invention;

FIG. 15 is a series of nine images of a focusing channel of an exemplary focusing device and a set of dots that depict electrolysis periods; and FIG. 16 is a graph depicting an exemplary generation of a two steps pH profile and an image of the exemplary focusing device.

DESCRIPTION OF EMBODIMENTS OF THE INVENTION

The present invention, in some embodiments thereof, relates to molecular analysis and interactions and, more particularly, but not exclusively, to methods and system for isoelectric focusing.

According to some embodiments of the present invention there are provided methods and systems for creating a stable graded pH gradient in an electrolyte solution so as to promote the concentration of biomolecules, such as proteins and peptides, according to their pI. The stable graded pH gradient has a plurality of steps, each having a different pH level. Each two sequential steps are separated by a steep pH ramp of more than 0.1 pH units, for example 0.5 pH units. Such a gradient allows concentrating biomolecules along the graded pH gradient in about 1000 seconds. Optionally, the stable graded pH gradient has less than 10 steps, for example 5, 4, 3, and 2.

According to some embodiments of the present invention, there is provided a focusing device for separating and/or diagnosing concentration of biomolecules. The device includes a focusing container, such as a focusing channel, for containing an electrolyte solution with a mixture of biomolecules. The device further includes electrodes for applying an electric field on the electrolyte solution. The electric field drives the biomolecules along an axis in the electrolyte solution. The focusing channel has one or more slits that allow one or more electrolysis units, referred to herein as pH generators, to inject $H^+$ or $OH^-$ ions into the focusing channel. The $H^+$ or $OH^-$ ions are generated by using bipolar membranes, optionally bubbleless. The $H^+$ or $OH^-$ ions shape a pH gradient along the axis. This allows biomolecules to concentrate along the pH gradient according to their pI.

According to some embodiments of the present invention there is provided a method for using image processing for computing the pH level in one or more segments of an electrolyte solution in a focusing container. In such an embodiment, pH indicator is added to the electrolyte solution. The pH indicator changes the color of the electrolyte solution along the focusing container according to a pH gradient which is formed therein. The changed color is captured using an image sensor. The captured data allows computing the pH level of one or more segments along the focusing container.

According to some embodiments of the present invention there is provided a removable solution cartridge that includes porous block for absorbing an electrolyte solution with a mixture of biomolecules. The porous block of the removable solution cartridge is sized and shaped to fit in a focusing channel, for example in a focusing channel as outlined above and described below. Optionally, in use, the porous block is wetted with the electrolyte solution and with a mixture of biomolecules to be separated and inserted into the focusing channel. Then, a pH gradient is created along the focusing channel together with a large electric field. The pH gradient promotes the concentration of biomolecules of the mixture in a number of concentrations along the porous block as biomolecule with different pIs concentrate in different places. Now, the porous block is extracted, allowing the user to segment the porous block, for example by pinching, in a manner that different concentrations are bounded in different segments.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
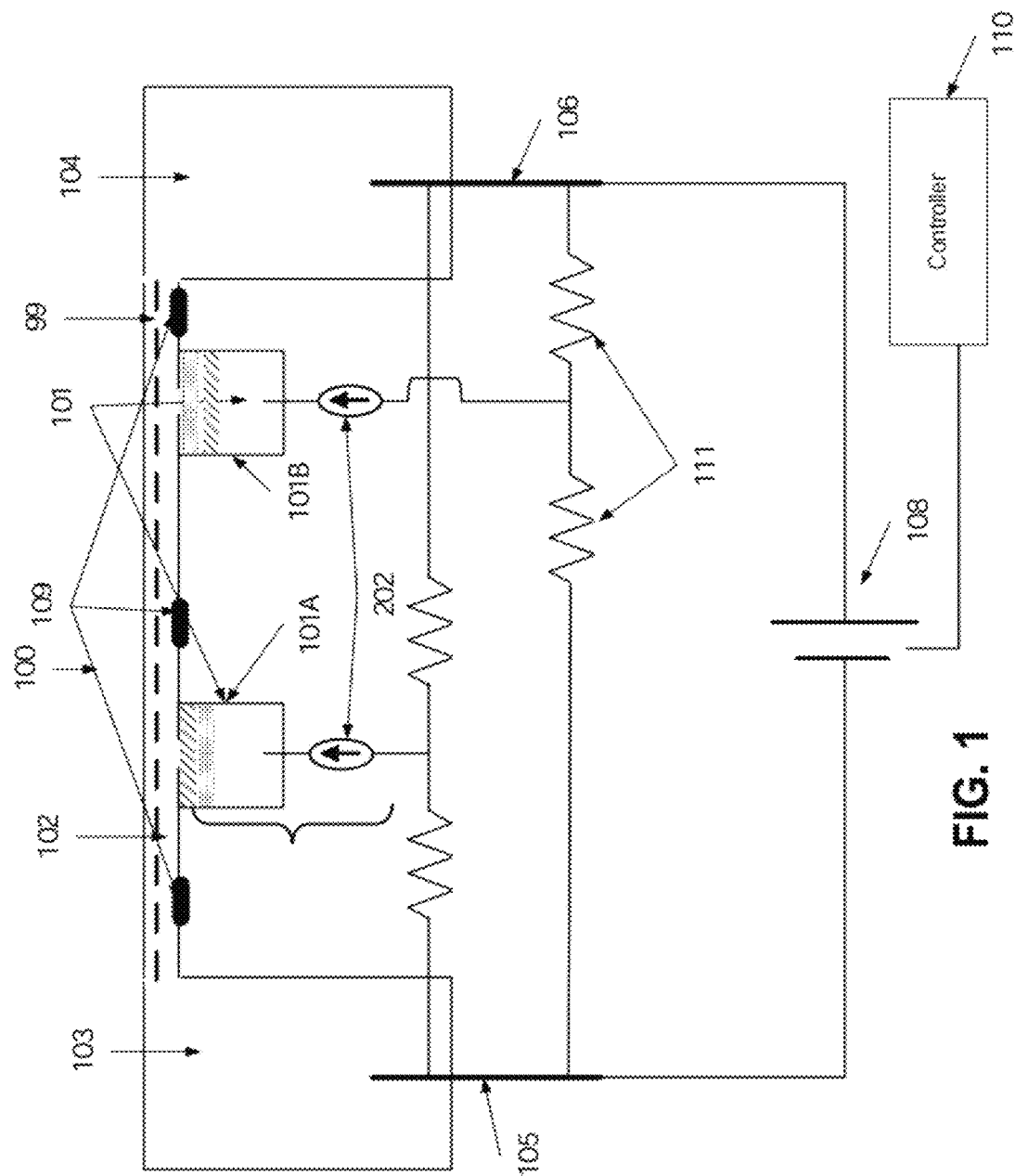

Reference is now made to FIG. 1, which is a schematic illustration of a lateral view of an exemplary isoelectric focusing device 100 for separating biomolecules in a mixture that includes one or more biomolecules and/or diagnosing an analyte having one or more biomolecules, according to some embodiments of the present invention. As used herein, biomolecules include proteins, peptides, peptide-based pharmaceutical compounds, and biomolecule based pharmaceutical compounds.

The isoelectric focusing device 100 includes a plurality of electrolysis units 101 which are optionally arranged as an array in a close proximity to a focusing container, referred to herein as a focusing channel 102. Optionally, the focusing channel is a rectangle glass capillary, for example 100 mm long, 5 mm wide and 0.5 mm thick. The electrolysis units 101 control the pH level at different segments along the longitudinal axis 99 of the focusing channel 102, or any other axis which is parallel thereto, by generating ion flow and injecting it into the focusing channel 102. These electrolysis units may be referred to herein as pH generators. In such a manner, a gradient having a plurality of pH grades which are separated from one another by steep pH ramps, created in the focusing channel 102 and optionally maintained for a period of more than few minutes, for example as long as ions are injected in the different segments. Such a gradient may be referred to a graded gradient and/or a pH gradient with a step shaped profile.

It should be noted that though only two pH generators are depicted, the isoelectric focusing device 100 may have any number of pH generators 101, for example, 4, 8, 12, 16, 20, 100 or any intermediate or greater number of pH generators 101.

As depicted in FIG. 1, each one of the left and right sides of the focusing channel 102 is open to an electrolyte solution receptacle 103, 104. One of the electrolyte solution receptacles 103 is connected to a cathode 105 and the other 104 is connected to an anode 106. The cathode and anode receptacles 103, 104 are optionally designed for high voltage (HV) and connect the focusing channel 102 to a main current source 108, optionally a HV current source, for example a power source having a voltage over approximately 300V. It should be noted that other electric fields may be applied depending on the mixture of biomolecules.

Optionally, the system 101 further comprises a controller 110 that controls the main current source 108 and the pH generators 101, optionally separately. For example, the electrodes of the pH generators 101 may be separately connected to the controller 110 in a manner that allows the controller to separately biasing each electrode, with a selected current.

Optionally, as depicted in FIG. 1, one or more pH probes 109 are placed along the focusing channel 102. Each pH probe 109 is located to monitor the local pH adjacently to one or more pH generators 101. Optionally, the controller receives the outputs of the pH probes 109. Optionally, the controller 110 receives the outputs of the pH probes 109 and adjusts the current that is forwarded to the pH generators 101 accordingly, for example as described in International Patent Application Publication No. WO 2009/027970, published on Mar. 5, 2009, which is incorporated herein by reference.

Figure 2:
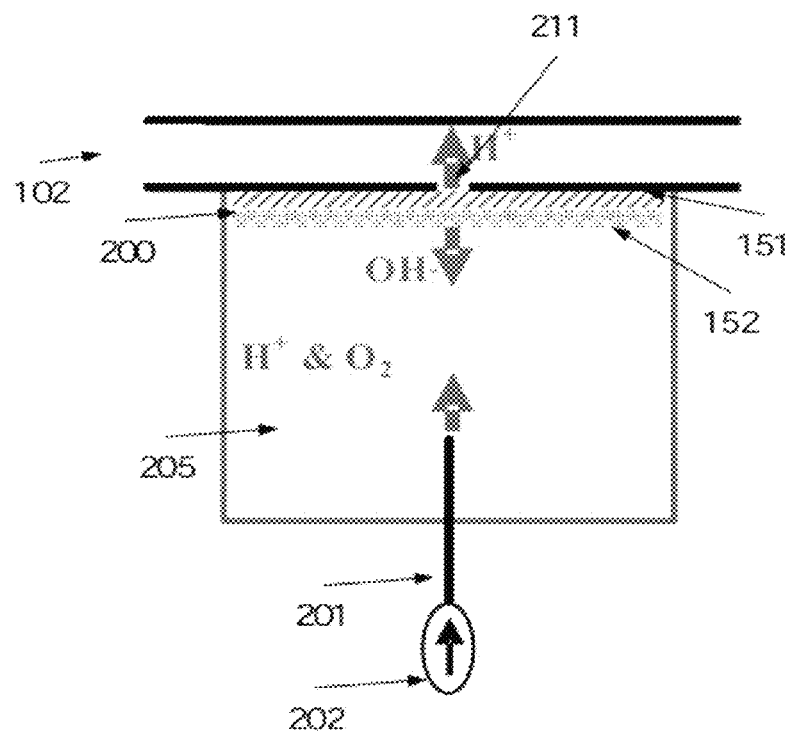

Reference is now also made to FIG. 2, which is a blow up of the exemplary pH generator 101 that is depicted FIG. 1, according to some embodiments of the present invention. The pH generator 101 comprises a bipolar membrane (BPM) 200 that is positioned in adjacent to the focusing channel 102. Optionally, the BPM is as defined in F. G. Wilhelm, I. et. al., Optimisation strategies for the preparation of bipolar membranes with reduced salt ion leakage in acid-base electrodialysis, Journal of Membrane Science 2001, 182 (1-2), 13-28, and G. Pourcelly, Electrodialysis with Bipolar Membranes: Principles, Optimization, and Applications, Russian Journal of Electrochemistry, 2002, 38(8), 919-926. The pH generator 101 further includes an electrode 201, such as a platinum electrode, which is connected to a generator current source 202 that is controlled by the controller 110. Optionally, the electrode 201 is a platinum wire that is connected to the generator current source 202. The electrode 201 is positioned in a space, for example 1 $cm^3$ in volume, optionally bounded, which may be referred to as a chamber 205. Optionally, the chamber 205 is filled with aqueous electrolyte solution.

Figure 3:
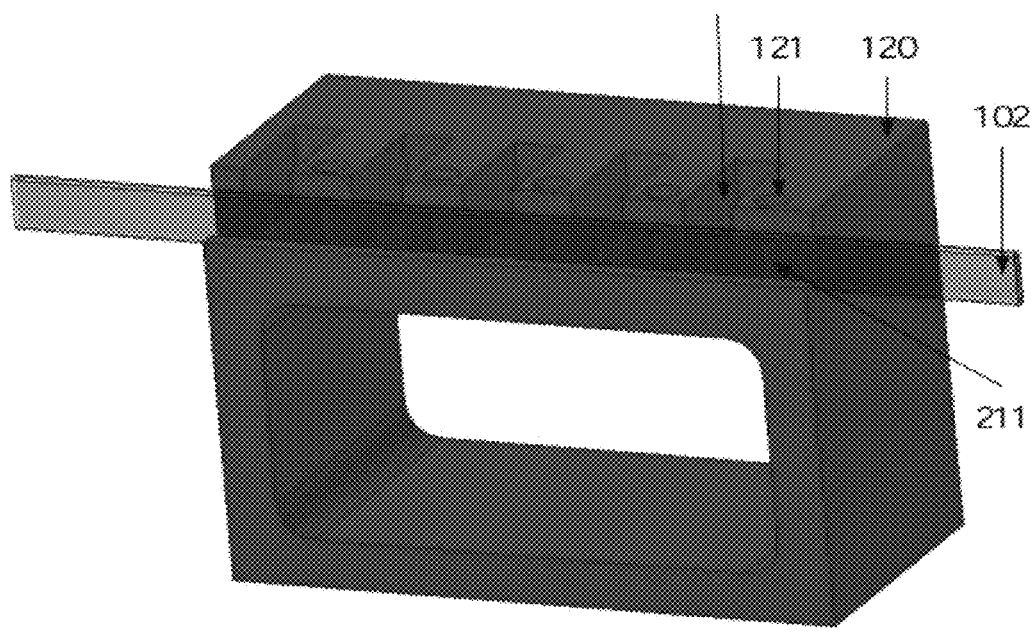

Reference is now also made to FIG. 3, which is a schematic illustration of an exemplary structure 120 for supporting the elements of the device 100, according to some embodiments of the present invention. Optionally, as outlined above, the channel is a rectangle glass capillary. The focusing channel 102 is mounted on the structure 120, which is optionally a Perspex block. The focusing channel 102 has thin slits 211 which allow passage of ions from the array of pH generators 101 and pH sensing from the pH probes 109. The structure 120 accommodates pH probe sockets into which the pH probes are inserted, as shown at 121 and generator chambers 205 in which the BPM 200 and the electrode 201 are inserted, for example as shown at FIG. 2. Optionally, each pH probe includes a Micro electrode 9070-008 of SENRON, which the specification thereof is incorporated herein by reference. The Micro electrodes are inserted into the pH probe sockets in which ions from the channel have a free passage to through a small slit, enabling the pH sensing.

According to some embodiments of the present invention, the generator current source 202 is connected to the anode 106 and the cathode 105, optionally through a Wheatstone bridge, for example as shown at 111 in FIG. 1. The Wheatstone bridge 111 is placed to connect between the cathode 105 and the anode 106. The Wheatstone bridge 111 is used to enable the pH generators 101 to work in high voltage. In the presence of a voltage of more than 10 volts, a potential difference may evolve between both sides of the BPM 200. In particular, a potential difference through the power supply 108 creates a potential difference between the two sides of the BPM. If the potential difference between the two sides of the BPM exceeds 10V, the PBM may be damaged. Such a potential difference may harm the BPM 200 as well as the generator current source 202. Optionally, the bridge consists of a series of resistors that balance the potential between the two sides of the membrane, reducing the potential difference between the two sides without preventing the operation of the BPM 200 and/or the generator current source 202. Alternatively, no high voltage is applied and the generator current source 202 is directly wired to the cathode 105 and the anode 106.

The pH generators 101, which may be energized by the generator current source 202, create a pH gradient in the focusing channel 102. The bipolar membrane 200 allows the pH generator 101 to efficiently dissociate water molecules into hydrogen $H^+$ and hydroxyl $OH^-$. As commonly known, a bipolar membrane have two sides, a side 151 that allows the releasing of $H^+$ and another side 152 that allows the releasing of hydroxyl $OH^-$. The BPM 200 may be positioned to release $H^+$ into the focusing channel 102 and hydroxyl $OH^-$ into the chamber 205, for example as shown at 101A, or in an inverse positioning so that to $OH^-$ is released into the focusing channel 102 and hydroxyl $H^+$ is released into the chamber 205, for example as shown at 101B.

Figure 4:
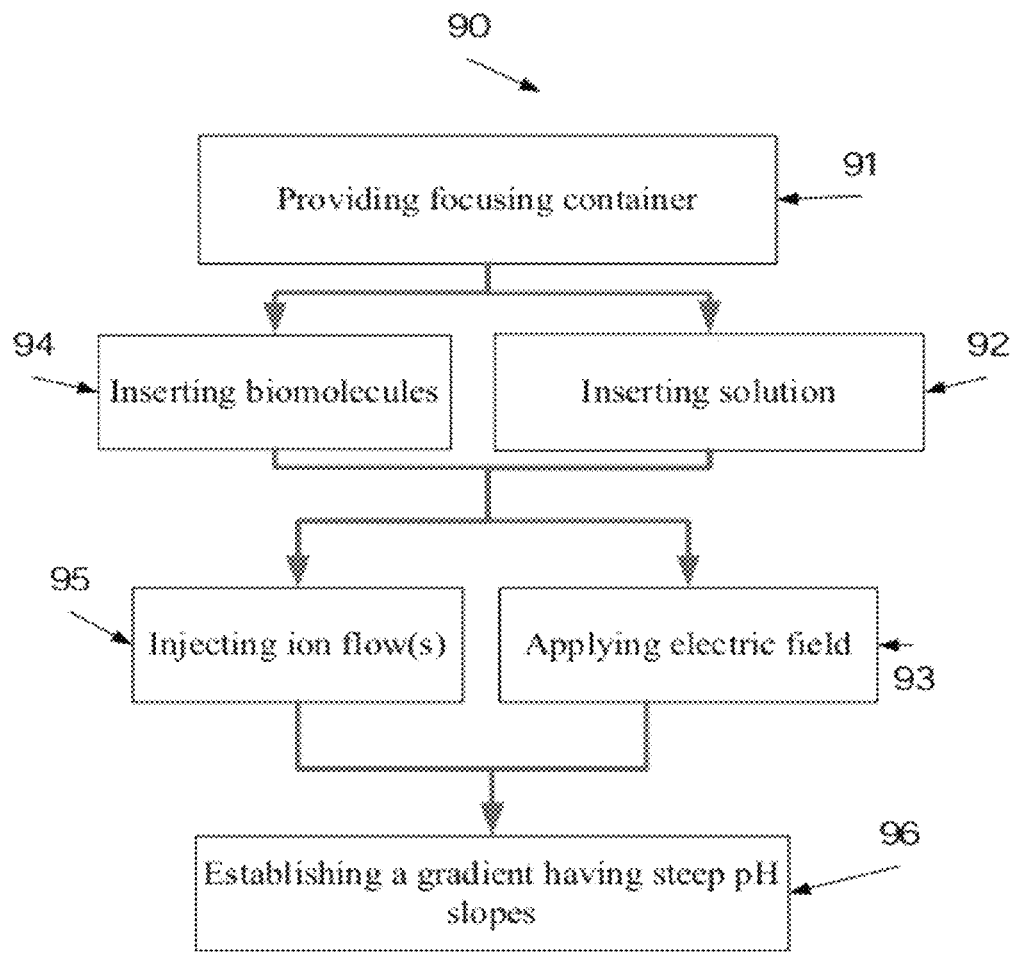

Reference is also made to FIG. 4, which is flowchart of a method 90 for isoelectric focusing, according to some embodiments of the present invention.

First, as shown at 91, a focusing container is provided, such as the container of the isoelectric focusing device shown at 100. Then, as shown at 92 an electrolyte solution fills the focusing container of the isoelectric focusing device. Optionally, the two electrolyte solution receptacles 103, 104 and the channel 102 are filled with solution. As shown at 94 a mixture of one or more different biomolecules, such as proteins, is added to the solution in the focusing container. It should be noted that the mixture may be added before and/or during the establishment of a pH gradient as described below. As shown at 93, an electric field, such as the aforementioned HV, is applied on the electrolyte solution along, the longitudinal axis 99, for example between the cathode 105 and the anode 106. Then, as shown at 95, one or more ion flows are injected in one or more points along the longitudinal axis 99 to establish, as shown at 96, a pH gradient defined by a plurality of steps which are separated by steep pH ramps so that the biomolecules accumulate in proximity to the injection points which create steep pH ramps in the space in front of the pH generators 101.

Figure 5:
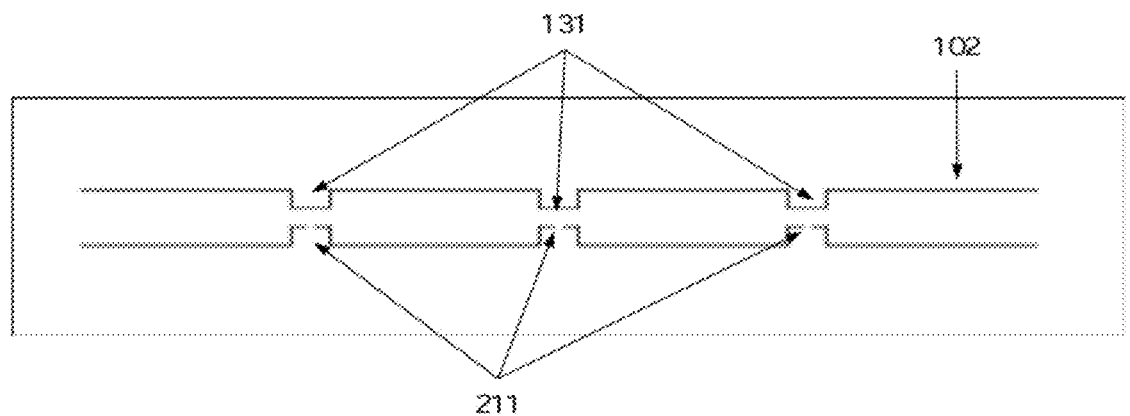

According to some embodiments of the present invention, the focusing channel 102 includes a number of narrowed segments having narrowed segments for increasing electric field in proximity to ion slits. In particular, as these segments are narrower than other segments of the channel, for example, as shown at numeral 131 of FIG. 5, the electric field that is formed therein is stronger than the electric field in other segments of the channel. In such an embodiment, the ion slits 211 are formed on the narrowed segments 131 of the channel 102. The strong electric field narrows the pH ramps so as to concentrate the biomolecules in a narrower segment of the channel.

Reference is now made to a description of a process of injecting hydrogen $H^+$ and/or hydroxyl $OH^-$ ions into the electrolyte solution in a manner that assure a stable pH gradient in the focusing channel 102. For clarity, the behavior of an ion of species i in electrolyte solution is governed by the following equation:

$$\partial C_i/\partial t + \vec{\nabla} \cdot (-D_{Ci} \vec{\nabla} C_i + z_i F \mu_{Ci} C_i \vec{E}) = R_i \qquad \text{Equation 1:}$$

where $C_i$ denotes the concentration of species i, $D_{Ci}$ denotes the diffusion coefficient of $C_i$, $\mu_{Ci}$ denotes the electrical mobility of $C_i$, $Z_i$ denotes the charge of $C_i$ in electron units, F denotes a faraday constant, $R_i$ denotes the reaction term of species i, and E denotes the electric field in the focusing channel 102. Basically, Equation 1 describes two driving forces which act on an ion in electrolyte solution, namely, diffusion and electric migration. In the device 100, the electric field is determined according to the HV current source 108 and therefore functions as a major driving force. According Poisson equation, the dependency of E on ion concentration may be described as follows:

Equation 2

$$\vec{\nabla} \cdot (\varepsilon \vec{E}) = 4\pi e \left( \sum_i z_i C_i \right) \qquad (2)$$

where $\in$ denotes the dielectric constant of water.

Optionally, in order to create a stable pH gradient in the presence of E in the focusing channel 102, an electrolyte solution abundant with one of the species ($H^+$ or $OH^-$) is derived through the channel. For instance, a pH 10 electrolyte solution may be derived through the channel with a concentration of $10^{-4}$M of $OH^-$ as the abundant species and $10^{-10}$M of $H^+$. In such an embodiment, the concentration of the abundant species may be gradually reduced by injecting other species along the focusing channel 102, for example $H^+$ ions.

Figure 7:
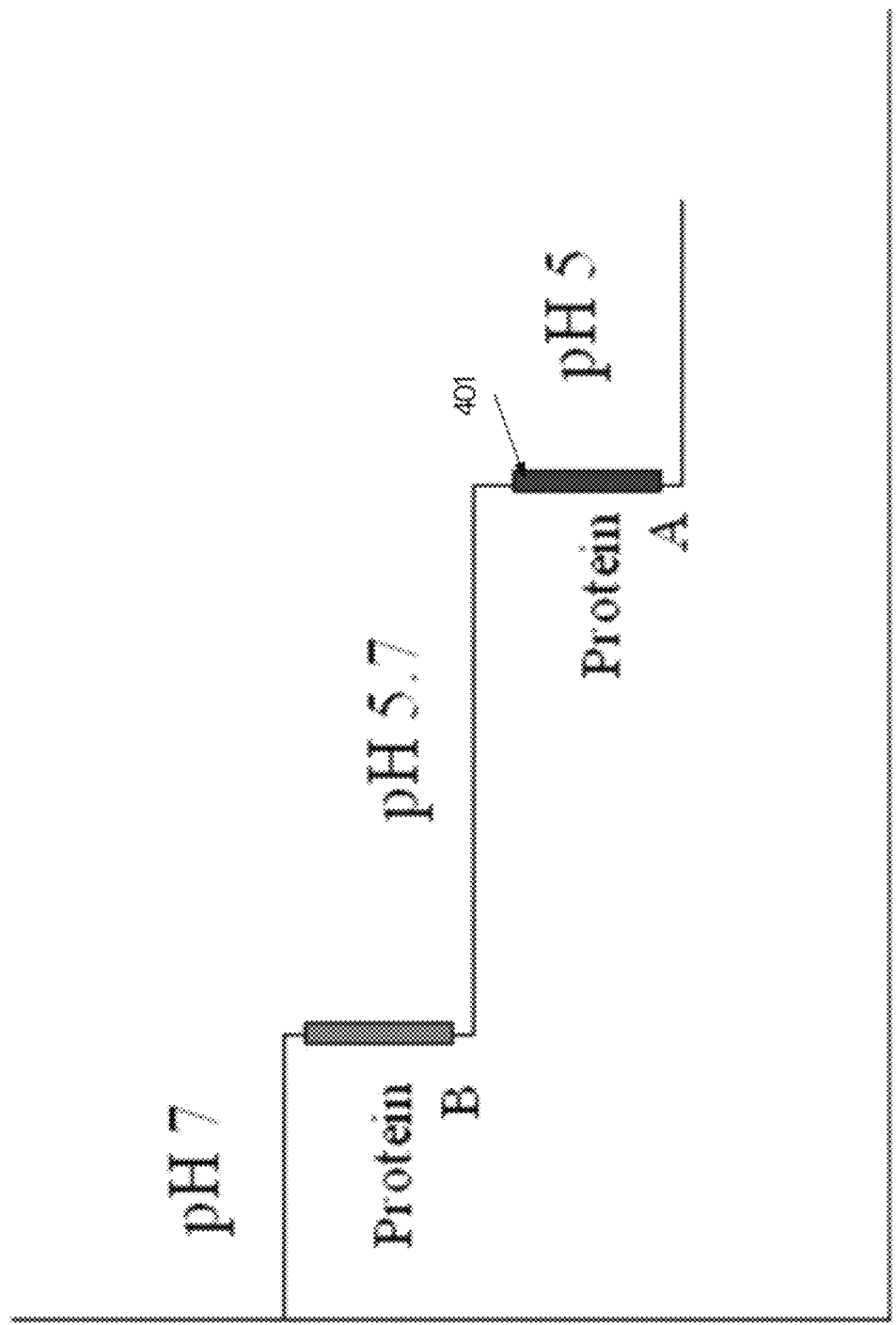

When the other species are injected into the focusing channel 102, a steep ramp in the pH level is created in the injection spot. The ramp is steep in relation to a constant pH value that is kept where no ion injection is performed. Briefly stated, such an injection creates a pH gradient having a step shape profile that defines exact spots were the analyst accumulate, namely, in front of the injectors. This makes the detection and/or harvesting of biomolecules easier. Optionally, the ratio between the ramp's length, the portion of the longitudinal axis of the focusing channel 102, and the ramp's height, the pH level change, is $10^{-4}$ m/1 pH unit In use, the injected biomolecules are driven until they arrive at a segment of the focusing channel 102 having a pH level that substantially or completely matches their pI. The graded gradient which is formed by the device 100, for example as shown at FIG. 7, allows expediting the focusing process. The driven force that is applied on biomolecules is stronger when the difference between the pH that surrounds them and their pI is greater. As the pH gradient of the electrolyte solution in the focusing channel 102 is divided to pH grades, the difference between the pI of biomolecules and the surrounding pH is relatively high until they arrive at a pH grade that has a pH that mostly, in relation to other grades, substantially or completely matches their pI. In the pH grade, biomolecules settle and concentrate at an area between two different pH grades. In such a manner, the velocity of the biomolecules in the focusing channel 102 is high and remains constant, unlike existing methods where the velocity reduces as the protein approaches its pI, and the focusing is relatively fast, for example 1000 seconds in a device 100 that produces a gradient with 2 steps.

On the other hand, in a pH gradient which is not step shaped, the driven force of the biomolecules decreases gradually with the gradual increase and/or decrease of the pH gradient. The focusing in such a gradient require a relatively long focusing time as the driven force of the biomolecules substantially reduces when they get closer to the point where the pH level matches their pI. Furthermore, the step shape profiles defines exact spots were the biomolecules accumulate, namely, in front of the injectors.

Optionally, the stability of the step shaped profile is maintained by adding a buffer with an acid dissociation constant (pKa) that is similar or identical to the step shaped pH profile of the electrolyte solution in the focusing channel 102. The value of the pKa preferably lies in the range of the pH levels of both sides of a steep pH ramp. For instance, to create a ramp between pH 5 and pH 6 steps, one should prefer a buffer with pKa between 5 and 6, for example 5.4. Optionally, a mixture of buffers with different pKa is added. In such a manner, a plurality of ramps may be stabilized simultaneously. An example of such a mixture is a mixture that includes 0.005M of $Na_2SO_4$ that function as a supporting electrolyte, 0.0025M phosphate buffer with a pKa of 2, 7.2, and/or 12.33, and 0.0025M Citrate with a pKa of 3.13, 4.76, and/or 640.

Figure 6:
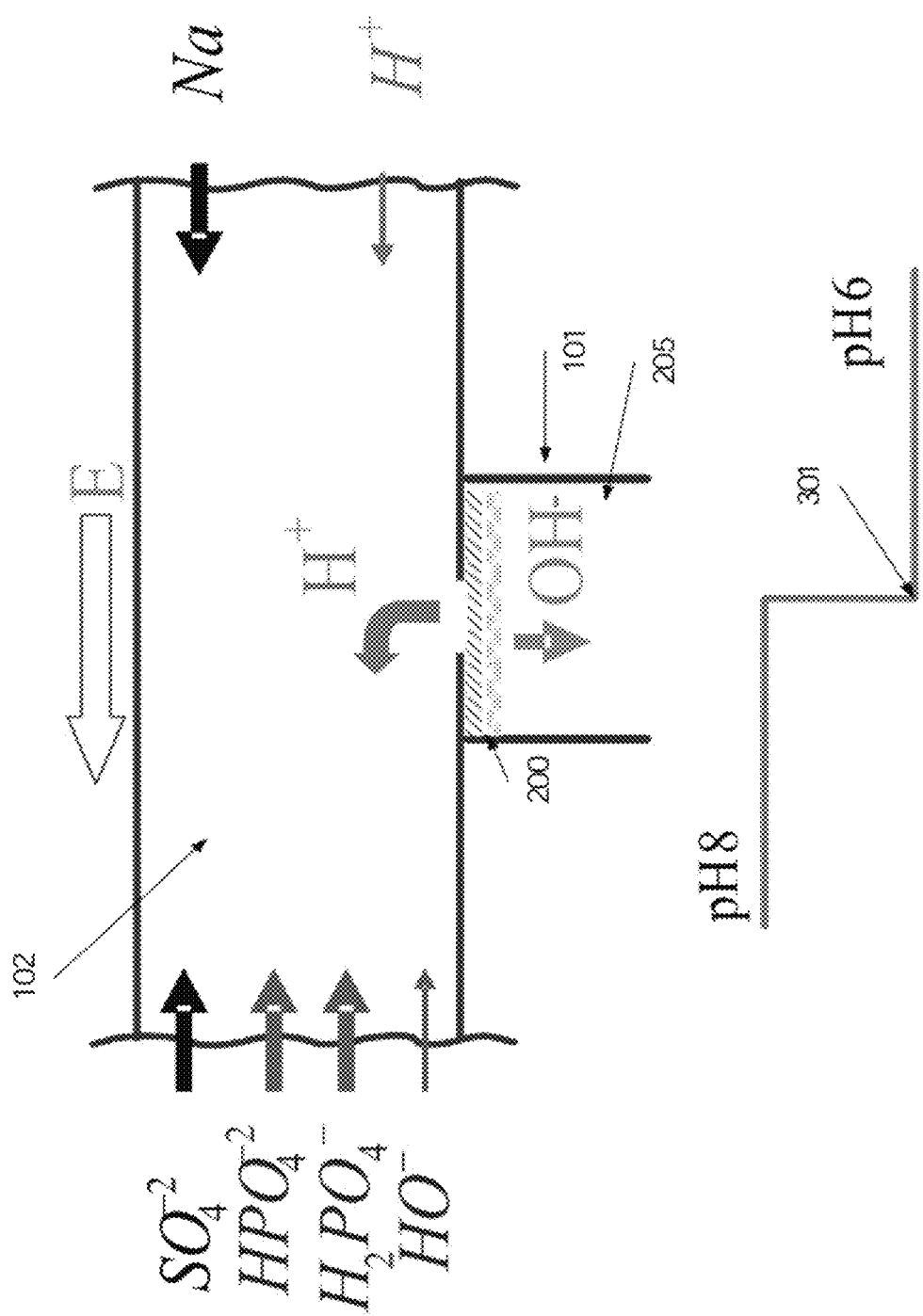

Reference is now made to FIG. 6, which is a segment of the focusing channel 102 that is positioned in proximity to a pH generator 101 and the step shaped gradient that is formed therein when using $Na_2SO_4$ electrolyte solution, according to some embodiments of the present invention. Optionally, a phosphate buffer at pH 8 is added to the $Na_2SO_4$ electrolyte solution. As depicted in FIG. 6, E drives positive ions (cations) to the left and the negative ions (anions) to the right. When the pH generator 101 is turned on, $H^+$ ions are injected into the focusing channel 102 and migrate immediately to the left while reacting with buffer ions. The concentration of $H^+$ and the buffer ions, created in response to the reaction, leads to a step shaped pH gradient, as shown at 301.

In this electrolyte solution, the species of the buffer molecules, which are present in high concentrations around the pH, are $HPO_4^{-2}$ and $H_2PO_4^-$. These buffer molecules participate in the following protonation reaction:

$$H^+ + HPO_4^{-2} \Leftrightarrow H_2PO_4^- \qquad \text{Equation 3:}$$

The dependency of the pH on the relative concentrations of $HPO_4^{-2}$ and $H_2PO_4^-$ may be represented, by the Henderson-Hasselbalch equation, as follows:

$$pH = pKa + \log\left(\frac{HPO_4^{-2}}{H_2PO_4^-}\right) \quad \text{Equation 4}$$

where Ka is the equilibrium constant of the reaction.

As commonly known, $H^+$ and $OH^-$ ions react to produce water $$H^+ + HO^- \Leftrightarrow H_2O \quad \text{Equation 5:}$$

with equilibrium constant Kw satisfying:

$$[H^+].[OH^-]=Kw=10^{-14}M^2 \quad \text{Equation 6:}$$

If the pH generator 101 is not turned on, the concentrations of all species are constant, and so is the pH level of the electrolyte solution. However, when one or more of the pH generators 101 inject protons to the focusing channel 102 they react, as shown at the forward reaction in Equation 3, where $HPO_4^{-2}$ ions are transformed to $H_2PO_4^-$ ions. Consequently, the pH level in the focusing channel 102 on the right hand side of the generator drops, as described in Equation 4. Thus, the injection of protons in each pH generator 101 creates the step shaped gradient by simultaneously changing the concentration of $H^+$, $H_2PO_4^{-2}$ and $H_2PO_4^-$ ions in the focusing channel 102. As E drives positive ions to the left and the negative ions to the right the concentration of $H^+$, $HPO_4^{-2}$ and $H_2PO_4^-$ on the left hand side of each pH generator 102 remains and the concentration of $H^+$ and $H_2PO_4^-$ and the concentration of $HPO_4^{-2}$ on the right hand side of the pH generator 102 respectively increases and decreases.

Its should be noted that the aforementioned step shaped pH profile may be generated in the absence of a buffer, when $H^+$ ions react with the $OH^-$, according to Equations 5 and 6. However, as $H^+$ and $OH^-$ ion concentrations may be small, for example between $10^{-6}$ and $10^{-8}$, relatively low currents may create steps in the profile. Such sensitivity causes every change in the provided current to affect or to eliminate the step shaped pH profile of a desired pH gradient in the focusing channel 102.

The pH generator 102 is energized in a manner that the flow of injected $H^+$ ions is lesser than the flow of the $HPO_4^{-2}$ ions. Otherwise, the flow of the $HPO_4^{-2}$ ions is wiped out by the flow of $H^+$ ions, causing a pH drop throughout the focusing channel 102.

Optionally, a number of pH generators 101 may be used for creating a graded pH profile. In such an embodiment, a plurality of pH generators 101, which are positioned along the focusing channel 102, produce a gradient multiple pH steps that may be controlled by different currents applied by the pH generators 101. Such a gradient with a graded profile may be utilized to simultaneously focus a plurality of biomolecules with different pIs. The controller may energize the pH generators 101 to establish different gradients having different step shaped pH profiles, each selected for probing and/or separating biomolecules of different mixtures. Each pH profile has segments with different pH levels. Each segment, which corresponds with a step in the graded pH profile, may be selected according to the pI of a different biomolecule in the mixture. In use, different biomolecules which are added to the electrolyte solution populate different segments of the focusing channel 102. Adding different biomolecules with different pIs to the focusing channel 102 may create a plurality of concentrations. For example, FIG. 7 depicts an exemplary gradient having a graded pH profile in which a first ramp has a pH level between 7 and 5.7 and a second ramp has a pH level between 5.7 and 5, created by the device 100 or the method 90 which are described above. The profile of the gradient is constructed so that the ramps match the pits of proteins A and B which have, respectively, a pI of 5.3 and 6. In such a manner, protein A settles down at the junction between pH 5 and 5.7 401 and protein B settles between pH 5.7 and 7. Such a pH profile may be used for separating a mixture of these biomolecules.

Reference is now made, again, to FIG. 2. As described above, the pH generator includes a BPM 200. As described above, the BPM 200 generates $H^+$ and $OH^-$ ions by splitting water molecules. Optionally, the BPM 200 includes one or more bubbleless membranes that do not produce blisters or bubbles thereon and/or therebetween during electrolysis. For brevity, such a BPM 200 may be referred to as a bubbleless BPM 200. When using such a bubbleless BPM 200, the focusing channel 102 remains substantially free from bubbles and therefore can be placed closer to the channel. Such proximity allows generating the pH gradient in a faster rate, for example in few seconds, and may remain stable for longer periods. Also, as the bubbleless BPM 200 allows generating a pH profile which is more accurate and stable than other pH generators, there are fewer fluctuations in the regions of the constant pH.

It should be noted that in order to prevent from bubbles to diffuse into a focusing channel when an electrode is used as a pH generator for example as described in International Patent Application Publication No. WO 2009/027970, published on Mar. 5, 2009, the electrode is placed in a distance from the focusing channel 102, for example 3 mm away. Such a distance delays the time it takes to ions generated by the electrode to travel to a typical focusing channel to create a pH gradient, for example to approximately 400 seconds. As described above, using a bubbleless BPM 200 prevents the generation of bubbles and therefore allows placing the pH generator 101 in a relatively close proximity to the focusing channel 102, for example less than 0.1 mm.

Furthermore, an array of such pH generators allows separating biomolecules in a greater resolution. The high stability of the gradient that is generated in such a device 100 allows separating biomolecules with a pI from a limited range.

Figure 8:
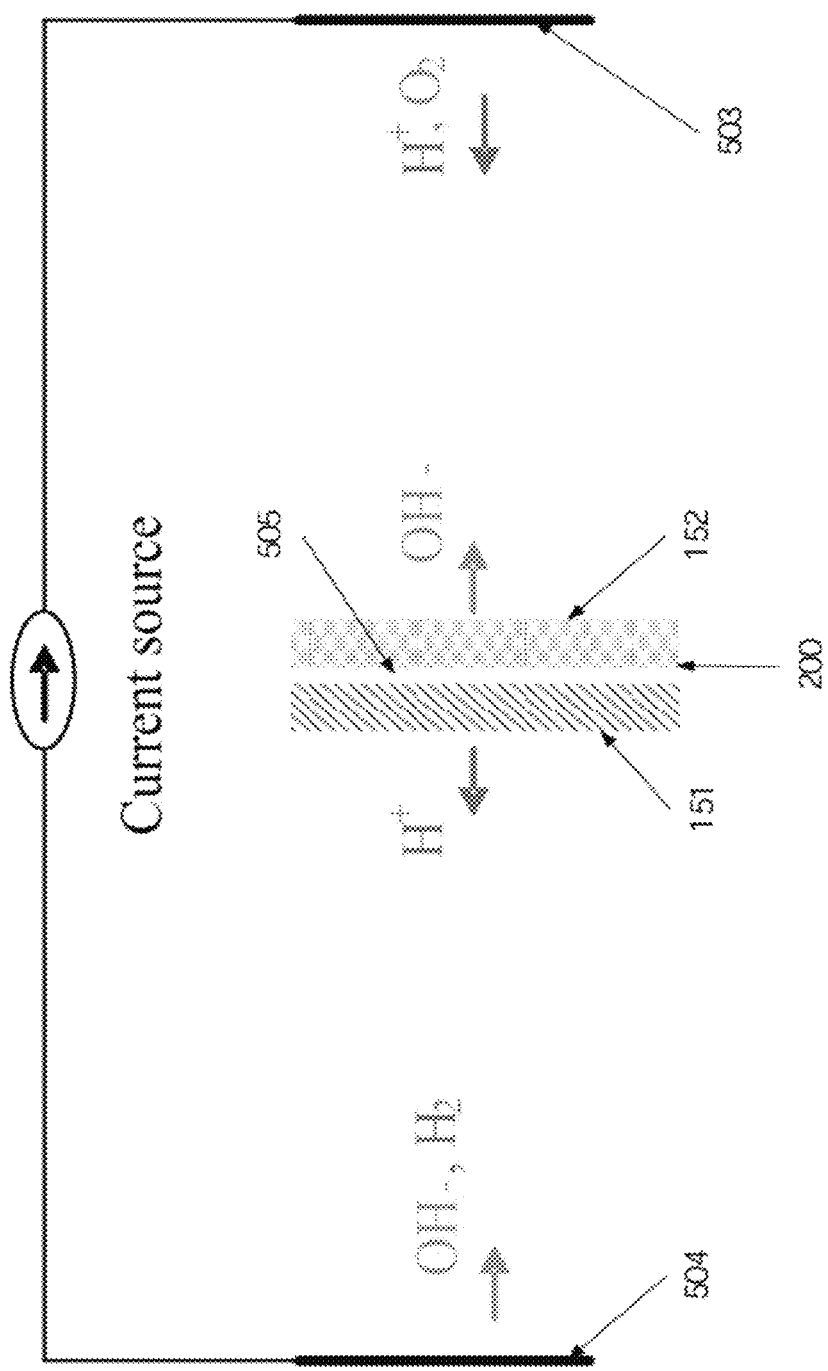

Reference is now made also to FIG. 8, which is a schematic illustration of a response of the bubbleless BPM 200 to a passing current, according to some embodiments of the present invention. The BPM 200 splits water molecules into $H^+$ and $OH^-$ ions. Optionally, the BPM consists of an anion-exchange layer 152 and a cation-exchange layer 151, which are placed in parallel to one another, leaving a thin interface 505 through which water may diffuse. The anion exchange layer 152 and the cation exchange layer 151 are semi-permeable membranes which respectively conduct anions and cations while being impermeable to ions of the opposite charge. The water electrolysis is achieved by placing the BPM 200 between an anode 503 and a cathode 504 so that the anion-exchange layer 152 faces the anode 503 and the cation-exchange layer 151 faces the cathode 504. Upon the appliance of voltage between the anode 503 and the cathode 504, water molecules between the layers 151 152 split, in opposite directions, into $H^+$ and $OH^-$ ions.

In addition to water splitting, water hydrolysis occurs, producing $H^+$ and $O_2$ gas molecules on the anode 503 and $OH^-$ and $H_2$ gas molecules on the cathode 504.

Reference is now made, once again, to FIG. 1. In use, a current generated by the main current source 108 creates a voltage difference between the cathode 105 and the anode 106 in the focusing channel 102. The pH generators 101, which are placed along the focusing channel 102, inject ions to the channel through small slits, for example approximately 0.5 mm, as shown in 211 of FIG. 3. As depicted in FIG. 1 each one of the electrodes of the pH generators 101 is connected to its respective generator current source 202 which, in turn, connects to the cathode 105 and the anode 106 through a Wheatstone bridge. In such a manner, the generator current source 202 drives current via the platinum electrodes of the pH generators 101 toward the cathode 105 and the anode 106 or vice versa. It should be noted, as described above, that the orientation of the BPM determines which ions are injected into the focusing channel 102.

In FIG. 1, with reference to a FIG. 8, the electrode of the left pH generator 101A functions as anode 503 and the cathode 105 and the anode 106 function, together, as cathode 504. pH generator 101A, and similar pH generators, has their bipolar membrane oriented so as to inject $H^+$ ions into the focusing channel 102. Such pH generators drive current from the respective electrode to the cathode 105 and to the anode 106. In contrary, the electrode of the right pH generator 101B functions as the cathode 504 and the cathode 105 and the Cathode 106 function, together, as the anode 503. pH generator 101B, and similar pH generators, has their bipolar membrane oriented so as to inject $OH^-$ ions into the focusing channel 102. Such pH generators drive current from the anode 105 and the Cathode 106 to the respective electrode.

Reference is now made, once again, to FIG. 2. As outlined above the chemical process that occurs inside the pH generator 101 allows injecting $H^+$ ions into the focusing channel 102. In use, as described above, current is driven via the electrode 201. The energized electrode 201 triggers electrolysis that breaks water molecules into $H^+$ and $O_2$ gas molecules. The current is driven to the cathode 105 and anode 106 where $OH^-$ and $H_2$ are generated. Between the electrode 201 and the cathode 105 and anode 106, the BPM 200 breaks water molecules into $H^+$ and $OH^-$ ions. As the electrode 201 and the BPM 200 are proximate to one another, the $OH^-$ ions produced by the BPM 200 and the $H^+$ produced by the electrode 201 continuously recombine according to Equation 5, and maintain a constant pH in the chamber. On the other hand, the distance between the cathode 105 and anode 106 and the BPM 200, allows controlling pH level in the focusing channel 102 for extended periods.

Figure 9:
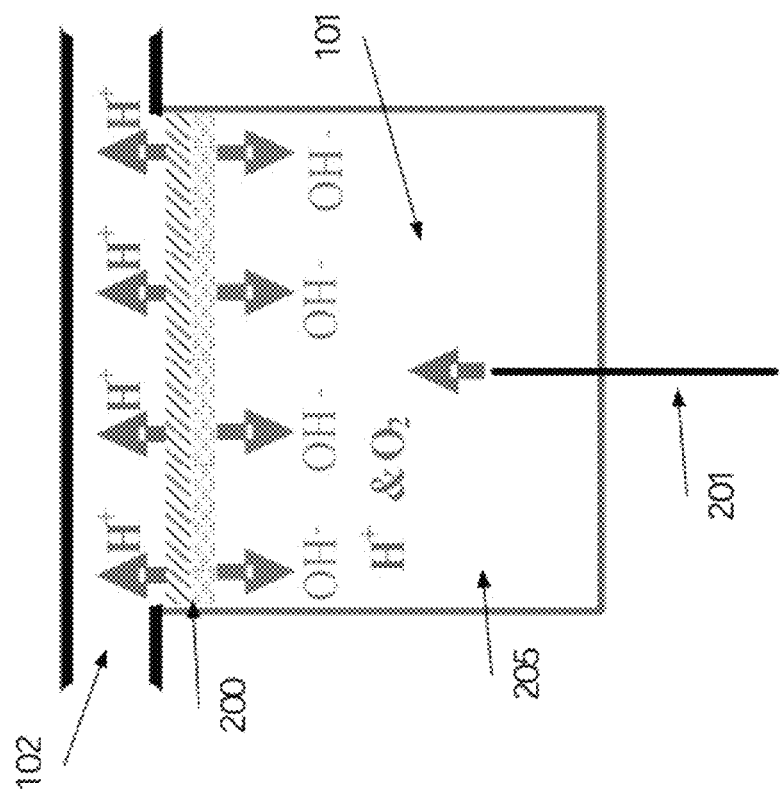

As the described above and depicted in FIG. 2, the pH generator 101 injects ions to the focusing channel 102 through the thin slit 211. Alternatively, the pH generator 101 injects ions through a wider opening, for example as shown in FIG. 9. In such an embodiment, the ions are injected via a slit which is a few cm wide. Since this setup is equivalent to a large number of thin slots placed very closely together, the result is a smooth pH profile made up of numerous short steps. In such an embodiment, the injection causes a pH profile having a moderate ramp that consist multiple small steps.

Reference is now made, once again, to FIG. 1. According to some embodiments of the present invention, the controller 110 is connected to a user interface (not shown), such as a module that includes a graphical user interface (GUI) executed on a client terminal, such as a personal computer or a laptop. In such an embodiment, the controller may energize the pH generators 101 according to values which are provided by the user. For example, the user may input a desired pH levels and the controller 110 may operate the pH generator accordingly. In another embodiment, the user selects one or more biomolecules and the controller 110 may operate the pH generator accordingly. In such an embodiment, the energizing is performed to create a pH profile that allows splitting the biomolecules in different segments of the focusing channel 102, for example as described above.

It is expected that during the life of a patent maturing from this application many relevant systems and methods will be developed and the scope of the term power source, GUI, and controller is intended to include all such new technologies a priori.

According to some embodiments of the present invention, the device 100 allows fixating biomolecule concentrations. As described above, the current that passes in the device 100 induces the injection of ions into the focusing channel 102 adjusts, optionally dynamically, its pH gradient in a manner that allows generating various biomolecule concentrations. However, when the current and the ion injection stop, these concentrations may dissolve. The dissolving limits the biomolecule concentrations diagnosis and/or harvesting of separated biomolecule concentrations and/or requires the maintaining of the current and the ion injection during the diagnosis period. Reference is now made to FIG. 10, which is a schematic illustration of the device 100 with a removable solution cartridge 119 having a porous block 118 that slows down or prevents the dissolving of the concentration, according to some embodiments of the present invention. The device 100 comprises all the elements depicted in FIG. 1, however, the focusing channel 102 forms a space for containing the removable solution cartridge 119 and an insertion opening for the inserting and/or extracting thereof. The porous block 118 is comprised from a porous material, for example cellulose. In use, the porous block 118 is wetted with the electrolyte solution and with a mixture of biomolecules for analysis and then is inserted into the focusing channel 102. Now, ions are injected by the pH generators 101, as described above. The porous material of the porous block 118 allows the injected ion to change the pH level therein, creating a pH gradient therealong, optionally having a graded profile, for example similarly to the described above. In such a manner, the aforementioned separation and focusing processes may take place within the porous block 118. When the focusing stabilizes, the porous block 118 may be segmented so as to allow isolating each one of the biomolecule concentrations. The segmentation may be performed by pinching, cutting, tying, and/or clamping intermediate areas that separate between different biomolecule concentrations in the porous block 118. For example, FIG. 11 schematically depicts the isolating of the biomolecules in an exemplary porous block 118. Numeral 131 is a detachable structure absorbed with a number of biomolecule concentrations and Numeral 132 is a pinched version thereto. Now, the segmented porous block 118 may be analyzed without passing current thereto for maintaining the biomolecule concentrations. Additionally or alternatively, the diagnosis and/or biomolecule harvesting may be performed for longer periods after the concentrations have been formed.

According to some embodiments of the present invention, the pH level in a focusing channel, such as the focusing channel 102 of the device 100, is measured according to color analysis. In such an embodiment, a pH indicator, such as litmus, Phenol red, bromcresol purple and/or any pH sensitive dye, are added into the electrolyte solution in the focusing channel 102. As the pH indicator in the electrolyte solution changes its color according to the pH levels in the focusing channel 102, image processing may be used for detecting the pH level. Optionally, an image sensor, such as a charge coupled device (CCD) and/or a complementary metal oxide semiconductor (CMOS) based sensors are used for capturing an image of the focusing channel and computing, by commonly known method of color analysis, one or more color properties of different segments of the focusing channel. The color properties allow calculating pH levels in the different segments according to said. Optionally, the determined pH level(s) are forwarded to the aforementioned GUI and presented to the user.

It should be noted that using image processing as described above allows receiving relatively fast pH level estimation. When Micro electrode based pH probes are used, a slit that facilitates contact between the micro electrode and the electrolyte solution is formed. The slits are connected to pH probe sockets into which the pH probes are inserted, for example as shown at 121 of FIG. 3. These sockets are filled with solution that allows the migration of ions from the channel, changing the pH level in the socket. The Micro electrode senses the pH level in the socket and allows estimating the pH level in a respective segment of the channel. However, as the migration of the ions into the socket takes time, a delay in the reading of the pH probe is induced. Furthermore, the sockets increase the required volume of the electrolyte solution and therefore increase the amount of ions which have to be injected into the channel during the process. Image sensors, on the other hand, do not require contact with the electrolyte solution and therefore no sockets are required. As the image sensor does not have to wait for ion migration the pH identification process becomes faster. In addition, as no sockets are required, the volume of the electrolyte solution may be reduced. Furthermore, as the image sensor is not in contact with the electrolyte solution, contaminations which are usually formed in elements which are placed in the solution may be reduced or avoided. In such a manner, the measurements which are performed by the image sensor are more reliable. In particular, probes which are based on pH electrodes tend to contaminate easily by the solution. This contamination adds an error to their readings. The image sensor is not exposed to such a contamination. Furthermore, HV currents pass in the channel 102. Such currents may damage probes which are in contact with the solution, such as pH electrodes. Using image sensors allows passing HV currents in the channel 101 without reducing the reliability and longevity of the system.

Reference is now made to FIG. 12, which is a schematic illustration of an electrophoresis container 192, having bipolar membranes 290 291 in opposing sides, which is designed to create a pH grading 292 that is transverse to the longitudinal axis of the electrophoresis container 192 in an electrolyte solution, according to some embodiments of the present invention.

The electrophoresis container 192, which is described in FIG. 12, allows creating a pH gradient, in an electrolyte solution it contains, between the opposing bipolar membranes 290 291. Different segments of the pH gradient have different pH levels, for example as described in Clyde A. Dubbs et. al., Science Jan. 28, 1966, Vol. 151. no. 3709, pp. 463-464, Transverse Gradient Electrophoresis: Protein Homogeneity Test and Subfractionation Technique, which is incorporated herein by reference.

The pH gradient 292, which may be referred to herein as a transverse pH gradient 292, allows separating proteins in a mixture that is placed in the electrophoresis container 192 without focusing them. The transverse pH gradient 292 is traverse to the direction of protein migration and perpendicular to an electric field 293 that is conducted through the electrophoresis container 192 so as to allow separating proteins in the mixture according to their mobility. As the mobility of a protein is pH depended, proteins of the same kind acquire different velocities depending on their ambient pH. The resulting separation pattern consist oblique lines along the channel.

The transverse pH grading 292 is created by the ions which are driven between the bipolar membranes 291, 292. In particular, as described above in relation to FIG. 8, the bipolar membrane consists of an anion-exchange layer 152 and a cation-exchange layer 151, which are placed in parallel to one another. The anion exchange layer 152 and the cation exchange layer 151 respectively conduct anions and cations while being impermeable to ions of the opposite charge. The water electrolysis is achieved by placing the bipolar membranes so that the anion-exchange layer 152 faces an anode and the cation-exchange layer 151 faces a cathode. Upon the appliance of voltage between the anode and the cathode, water molecules between the layers 151 152 split, in opposite directions, into H+ and OH− ions. The flow of H+ ions that is created between the bipolar membranes 291, 292 creates the pH gradient.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Reference is now made to the following example, which together with the above descriptions, illustrates some embodiments of the invention in a non limiting fashion.

The example is based on a simulation of an exemplary focusing device that uses a single pH generator for producing a step shaped pH profile, for example as described above in relation to FIGS. 1 and 2. The simulated pH generator is based on a bubbleless BPM, as described above. It should be noted that though the simulated exemplary focusing device includes a single pH generator, any number of pH generators may be used, as described above. The simulation is performed by solving a set of partial differential equations (PDEs). This set includes Equation 2 and a subset of equations of the form of Equation 1, each equation is defined per species in the electrolyte solution. Appropriate boundary conditions are constant concentrations on both sides of the focusing channel of the exemplary focusing device and a constant current of $H^+$ ions from a pH generator, for example as depicted in FIG. 2 and described above. Initial conditions are added as constant concentrations anywhere in the exemplary focusing device. The complete set of equations is as follows:

$$\nabla \cdot \vec{E} = 1.4 \times 10^{14}([Na^+]+[H^+]-[OH^-]-2[SO_4^{-2}]-2[HPO_4^{-2}]-[H_2PO_4^-])$$

$$\partial[Na^+]/\partial t + \vec{\nabla} \cdot (-D_{Na^+}\vec{\nabla}[Na^+]+F\mu_{Na^+}[Na^+]\vec{E}) = 0$$

$$\partial[SO_4^{-2}]/\partial t + \vec{\nabla} \cdot (-D_{SO_4^{-2}}\vec{\nabla}[SO_4^{-2}]-2F\mu_{SO_4^{-2}}[SO_4^{-2}]\vec{E}) = 0$$

$$\partial[H^+]/\partial t + \vec{\nabla} \cdot (-D_{H^+}\vec{\nabla}[H^+]+F\mu_{H^+}[H^+]\vec{E}) = k_w([H^+] \cdot [OH^-]-Kw+[H^+] \cdot [HPO_4^{-2}]-Kp[H_2PO_4^-])$$

$$\partial[OH^-]/\partial t + \vec{\nabla} \cdot (-D_{OH^-}\vec{\nabla}[OH^-]-F\mu_{OH^-}[OH^-]\vec{E}) = -k_w([H^+] \cdot [OH^-]-Kw)$$

$$\partial[HPO_4^{-2}]/\partial t + \vec{\nabla} \cdot (-D_{HPO_4^{-2}}\vec{\nabla}[HPO_4^{-2}]-2F\mu_{HPO_4^{-2}}[HPO_4^{-2}]\vec{E}) = -k_p([H^+] \cdot [HPO_4^{-2}]-Kp[H_2PO_4^-])$$

$$\partial[H_2PO_4^-]/\partial t + \vec{\nabla} \cdot (-D_{H_2PO_4^-}\vec{\nabla}[H_2PO_4^-]-F\mu_{H_2PO_4^-}\vec{E}) = -k_p([H^+] \cdot [HPO_4^{-2}]-Kp[H_2PO_4^-])$$

where Kw and kw denote equilibrium and association rate constants for the reaction shown in Equation 5, and Kp and kp denote equilibrium and association rate constants for the reaction shown in Equation 3.

Such a simulation provides results as shown in FIGS. 11 and 12, each depicts a graph of pH profiles created in the presence of a high electric field and a pH generator current positioned at x=0. FIG. 13 depicts pH profiles at various times where $E=10^{-6}$ mol/m$^2$ s and FIG. 14 depicts steady state pH profiles, an outcome of various currents.

FIG. 13 depicts a pH profile that evolves as a function of time, in the presence of a pH generator passing a constant current ($10^{-6}$ mol/m$^2$s) and positioned at x=0. As depicted in FIG. 11, an acidic front advances so as to create a profile with a sharp pH step within seconds. An acidic regime of 5 mm long is created in approximately 100 sec on the right while on the left the initial pH level is maintained. FIG. 14 shows gradients having steady state pH profiles in various magnitudes of currents. As seen, the magnitude of the current determines the height of the pH step.

Reference is now made to an example that exemplifies the generation of a pH gradient by the exemplary focusing device used in the example described in relation to FIGS. 11 and 12. As used herein, a pH gradient generation rate means the period it takes a pH gradient to stabilize in the focusing channel of the exemplary focusing device. As depicted in FIG. 13, a single-step pH profile is created by the pH generator of the simulated exemplary focusing device. In order to appreciate the pH gradient generation rate of the exemplary focusing device, the pH gradient of the exemplary focusing device has been monitored in a number of instances during a period. FIG. 15 is a series of nine images of the focusing channel of the exemplary focusing device and a set of dots that depict electrolysis periods. The images were sequentially captured with a minute interval between them in a period t of 8 minutes. A pH indicator was added to the electrolyte solution in the exemplary focusing device. Numerals 901-903 shows 3 pH probes (black sticks) inserted therealong. Numeral 904 indicates the pH generator. The applying of current by the pH generator is indicated by a filled dot and the absence of current is indicated by an unfilled dot. The electrolyte solution, with the pH indicator, turns purple if the pH level is above 7 or red if it below 4.5. At t=0.5, the pH generator of the exemplary focusing device was energized, drawing a current of 80 μA. As a consequence, H+ ions were injected to the focusing channel creating an acidic front which advanced to the right, as the simulations depicted in FIGS. 11 and 12 predicts. At t=4.5 min, the current was turned off, and the acidic regime vanished. At t=6.5 min, the pH generator was energized again and the acidic regime evolved once more. As depicted in the images, a sharp pH increment is indicated by a color change at the segment between pH probe 902 and pH probe 903, while the color of the segment between 902 and 901 remains constant all along the 8 minutes, indicating a pH level 8.

The sharp pH increment may also be indicated by FIG. 16 that is a graph 1005 depicting an exemplary generation of a two steps pH profile and an image 1006 of the exemplary focusing device described above. The image shows the channel 1001, the pH generator 904 and the pH probes 901-903, and the electric field direction 1007. The graph depicts the readings of probes 901-903 as a function of time. As depicted, pH probe 903 reads a continuously decreasing pH level indicating a formation of an acidic regime on the right hand side of the pH generator. pH probes 901 and 902 read a substantially constant pH level indicating a constant pH level that is not affected by the applied current. The initial generator current was 100 μA and was later raised to 110 μA and 120 μA.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for isoelectric focusing, comprising:
providing a focusing container having a channel along a longitudinal axis, said channel is configured to contain an electrolyte solution, said focusing container having a plurality of electrolysis units, distributed along said longitudinal axis, each having at least one electrode; and
receiving an input defining any of a plurality of desired pH gradients having a plurality of steps in said electrolyte solution along said longitudinal axis;
separately controlling the energizing of each of said plurality of electrolysis units according to said desired pH gradient to induce the injecting of either an ion flow or a proton flow into said focusing container via a membrane as an outcome of an electric field formed with respective said at least one electrode so as to create said pH gradient;
wherein each said step having a substantially uniform pH level along said longitudinal axis, each one of said plurality of desired pH gradients being defined by at least one pH ramp between every two sequential steps of said plurality of steps.

2. The method of claim 1, wherein said pH gradient is defined by a plurality of ramps among said plurality of steps, further comprising adding a mixture of buffers for stabilizing said pH gradient.

3. The method of claim 1, wherein said membrane is a bipolar membrane.

4. The method of claim 1, further comprising diagnosing a plurality of biomolecules arranged according to said pH gradient.

5. The method of claim 1, further comprising separately harvesting a plurality of biomolecules arranged according to said pH gradient.

6. The device of claim 3, wherein said at least one bipolar membrane consists of an anion-exchange layer and a cation-exchange layer placed in parallel to one another; wherein said anion-exchange layer is oriented so as to conduct anions while being impermeable to cations.

7. The device of claim 6, wherein said cation-exchange layer is oriented so as to conduct cations while being impermeable to anions.

8. A device for isoelectric focusing, comprising:
a focusing container having a channel formed along a longitudinal axis, said channel is configured to contain an electrolyte solution; and
a plurality of electrolysis units, distributed along said longitudinal axis and mounted externally to said channel, in a close proximity to said longitudinal axis, each said electrolysis unit having at least one electrode and being configured to inject either an ion flow or a proton flow into said channel of said focusing container via a membrane and;
a controller configured to separately control the energizing of each of said plurality of electrolysis units according to any of a plurality of desired pH gradients along said longitudinal axis, each one of said plurality of desired pH gradients having a plurality of steps in said electrolyte solution along said longitudinal axis, each said step having a substantially uniform pH level along said longitudinal axis, each one of said plurality of desired pH gradients being defined by at least one pH ramp between every two sequential steps of said plurality of steps.

9. The device of claim 8, wherein said pH ramp is of at least 0.1 pH.

10. The device of claim 8, wherein each said step is at least 3 mm long.

11. The device of claim 8, wherein said electrolyte solution comprises a plurality of biomolecules, said plurality of biomolecules concentrating only at said at least one pH ramp along a respective said pH gradient.

12. The device of claim 8, wherein one of said at least one electrolysis unit is configured to inject a plurality of Hydroxyl ions and another of said at least one electrolysis unit being configured to inject a plurality of Hydrogen ions.

13. The device of claim 8, wherein said channel of said focusing container has a plurality of narrowed segments, each said electrolysis unit being configured to inject said ion flow in a respective said narrow segment.

14. The device of claim 8, wherein said membrane is a bipolar membrane.

* * * * *